(12) United States Patent
Wilson

(10) Patent No.: US 7,229,820 B2
(45) Date of Patent: Jun. 12, 2007

(54) APPARATUS AND METHOD FOR CULTURING AND PRESERVING TISSUE CONSTRUCTS

(75) Inventor: John R. Wilson, New Brighton, MN (US)

(73) Assignee: Wilson Wolf Manufacturing Corporation, New Brighton, MN (US)

( * ) Notice: Subject to any disclaimer, the term of this patent is extended or adjusted under 35 U.S.C. 154(b) by 265 days.

(21) Appl. No.: 10/460,850

(22) Filed: Jun. 13, 2003

(65) Prior Publication Data

US 2004/0043481 A1   Mar. 4, 2004

Related U.S. Application Data

(60) Provisional application No. 60/388,567, filed on Jun. 13, 2002.

(51) Int. Cl.
*C12M 1/00* (2006.01)
(52) U.S. Cl. .............................. 435/284.1; 435/297.1; 435/1.3
(58) Field of Classification Search ................. None
See application file for complete search history.

(56) References Cited

U.S. PATENT DOCUMENTS

| | | | |
|---|---|---|---|
| 4,485,096 A | 11/1984 | Bell | |
| 4,569,853 A * | 2/1986 | Strobel | 426/599 |
| 4,835,102 A | 5/1989 | Bell et al. | |
| 5,266,480 A | 11/1993 | Naughton et al. | |
| 5,282,859 A | 2/1994 | Eisenberg | |
| 5,536,656 A | 7/1996 | Kemp et al. | |
| 5,686,304 A | 11/1997 | Codner | |
| 5,707,869 A * | 1/1998 | Wolf et al. | 435/401 |
| 5,766,937 A | 6/1998 | Lahm et al. | |
| 5,863,531 A | 1/1999 | Naughton et al. | |
| 6,039,760 A | 3/2000 | Eisenberg | |
| 6,121,042 A | 9/2000 | Peterson et al. | |
| 2003/0157709 A1 | 8/2003 | DiMilla et al. | |

FOREIGN PATENT DOCUMENTS

| | | | |
|---|---|---|---|
| WO | WO 0024437 | * | 5/2000 |
| WO | WO 02/38460 A1 | | 5/2002 |
| WO | WO 03/060061 A1 | | 7/2003 |

OTHER PUBLICATIONS

Leighton et al., J. Natl. Cancer Inst., 1951, 12:545-561.
Leighton et al., Cancer Res., 1968, 28:286-296.
Sorour et al., J. Neurosurg., 1975, 43:742-749.
Yang et al., Cancer Res., 1981, 41:1021-1027.
Tun et al., ASAIO, 2000, 46(5), 522-526.

* cited by examiner

*Primary Examiner*—James Ketter
(74) *Attorney, Agent, or Firm*—Patterson, Thuente, Skaar & Christensen, P.A.

(57) ABSTRACT

A disclosure is made of various apparatus and methods for culturing and preserving cells and tissue in ways that minimize contamination potential, direct cells to reside in desired areas, allow uniform cell distribution during seeding, provide optimal growth conditions by controlling the amount of medium residing in proximity of cells, allow desired compounds and molecules to reside in proximity of the cells, allow co-culture, provide for efficient scale up, allow a desired shape of tissue to be created while retaining a closed system, and allow cryopreservation and reconstitution of cell and tissue while retaining a closed system. The apparatus and methods can be combined to prevent the need to remove the tissue from the enclosure at any point during the sterilization, seeding, culturing, cryopreservation, shipping, or restoration process. Also disclosed is an apparatus and method of pipette interface with a container in a manner that blocks contaminants from entering the container.

20 Claims, 13 Drawing Sheets

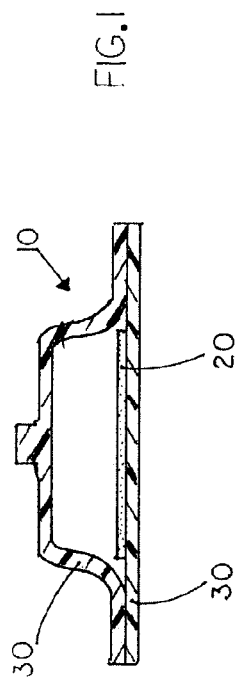
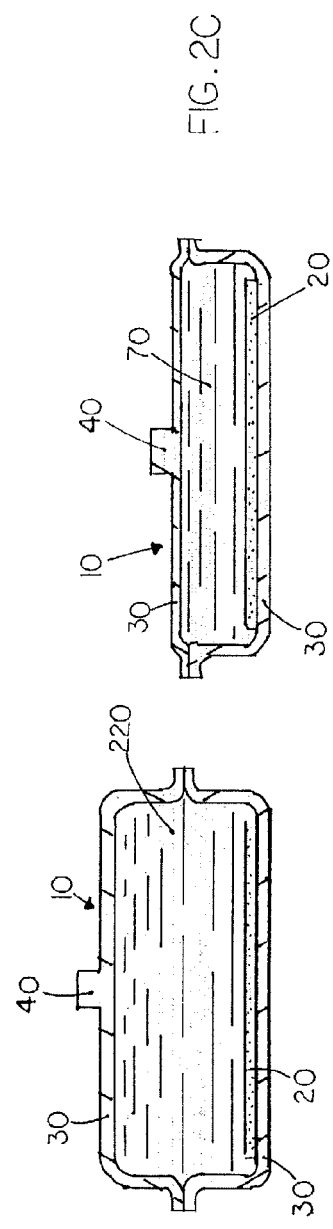
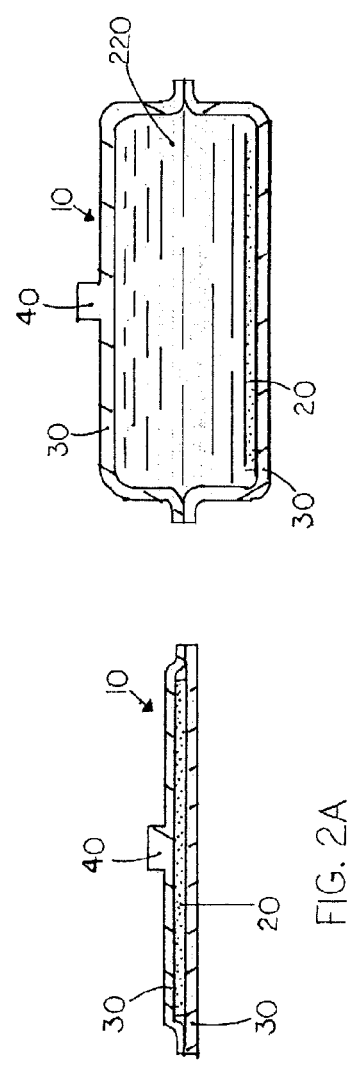
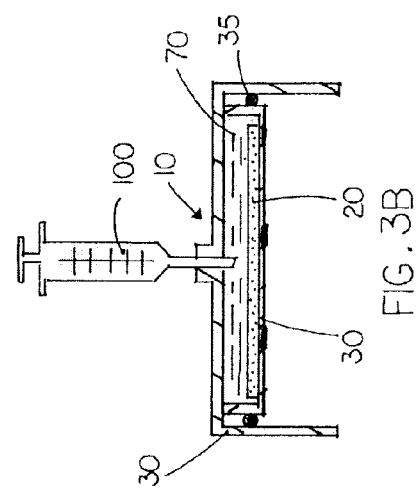
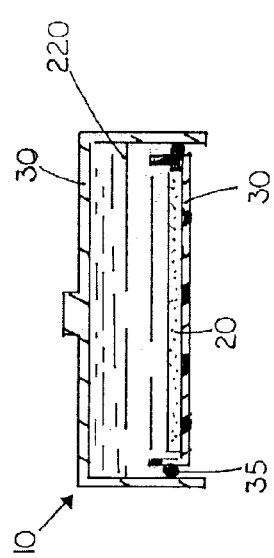

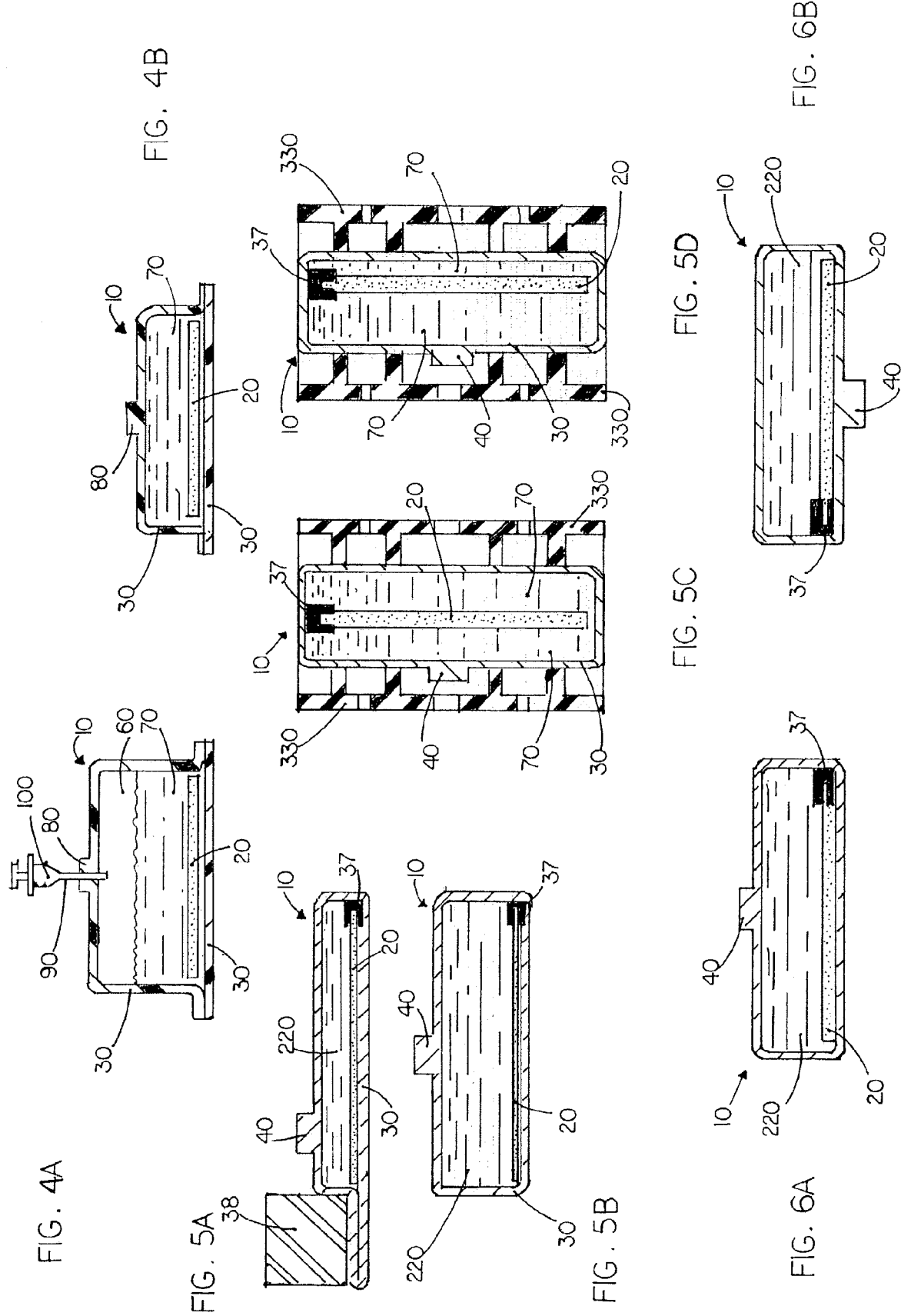

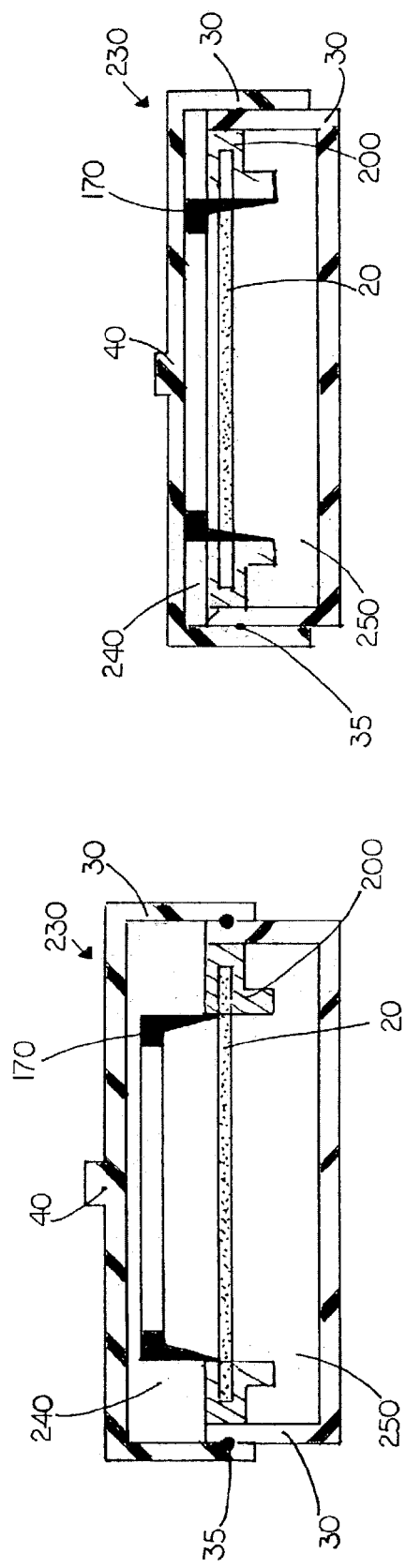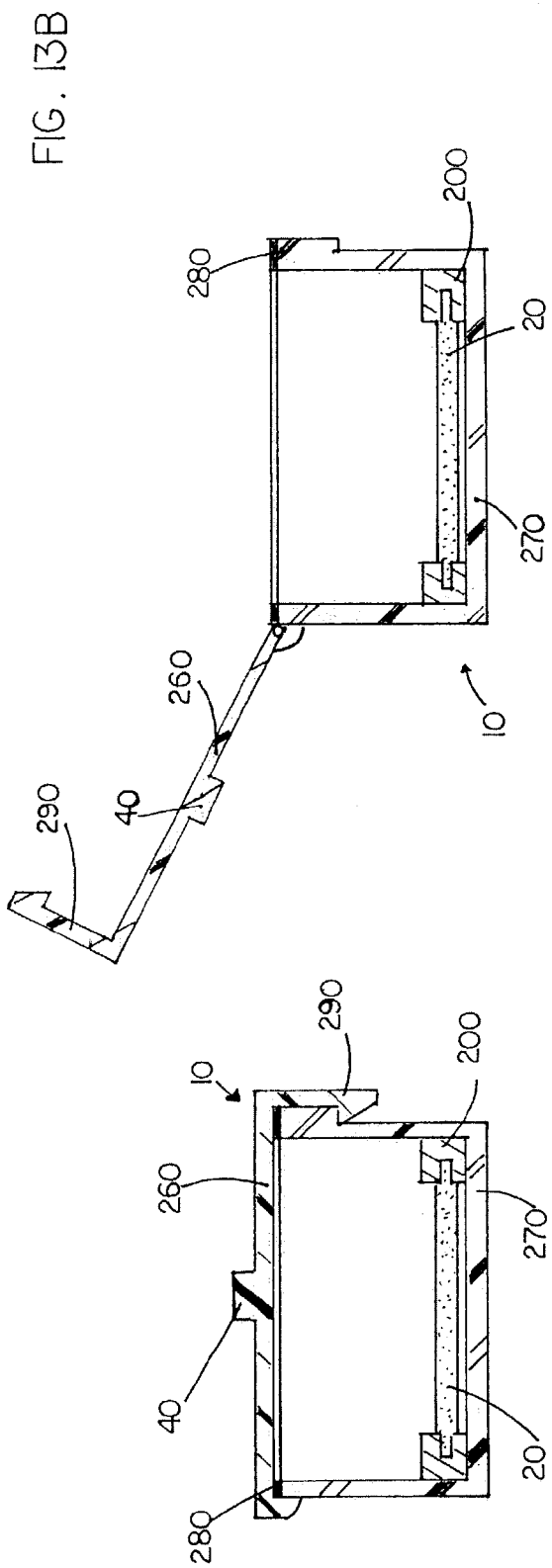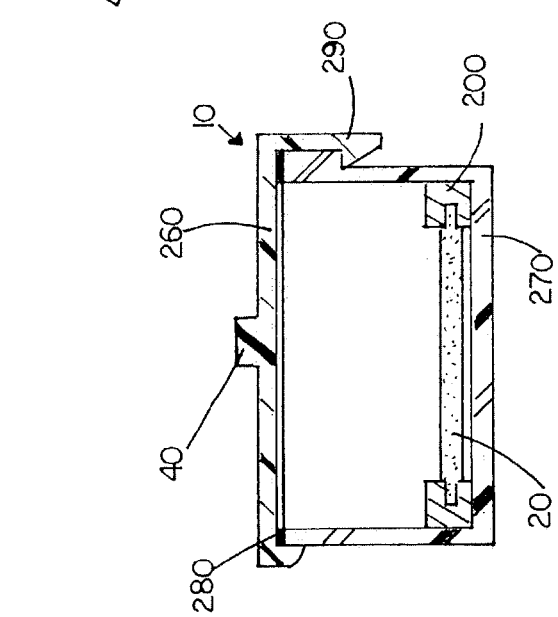

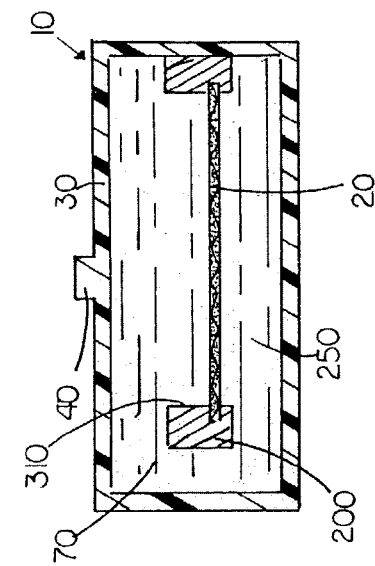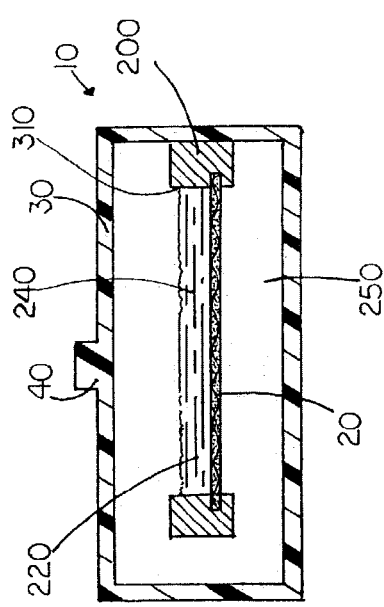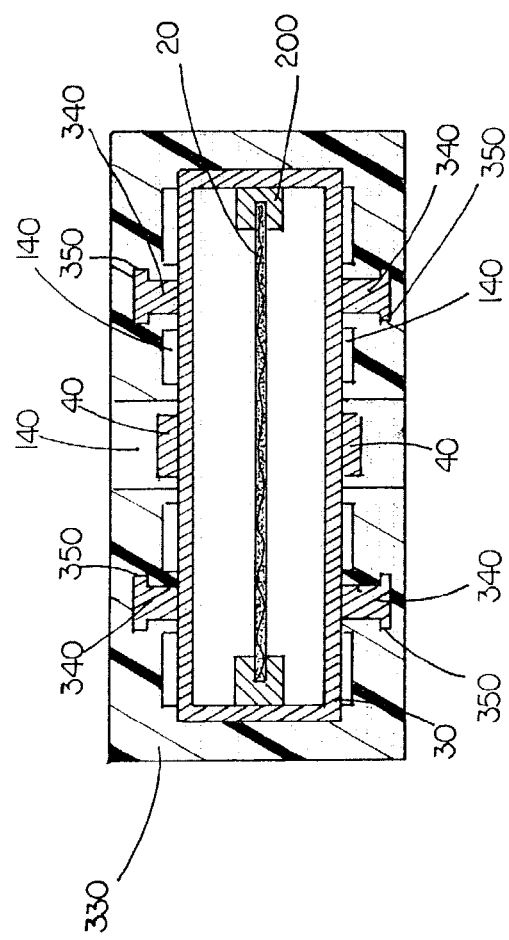

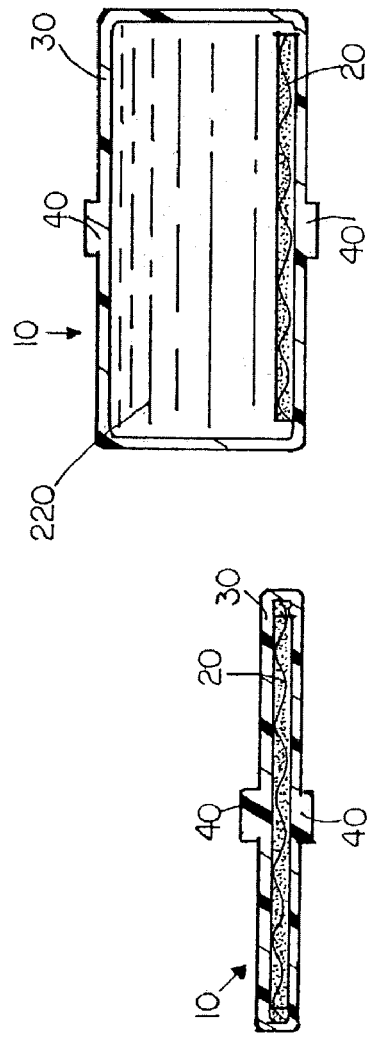
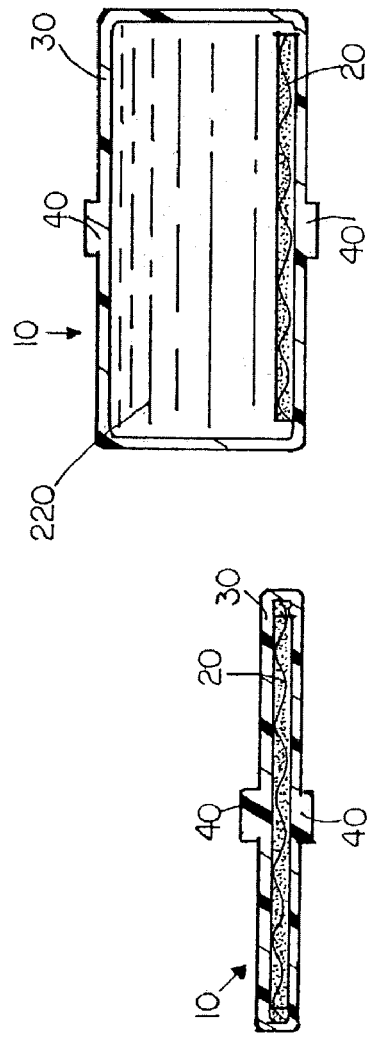
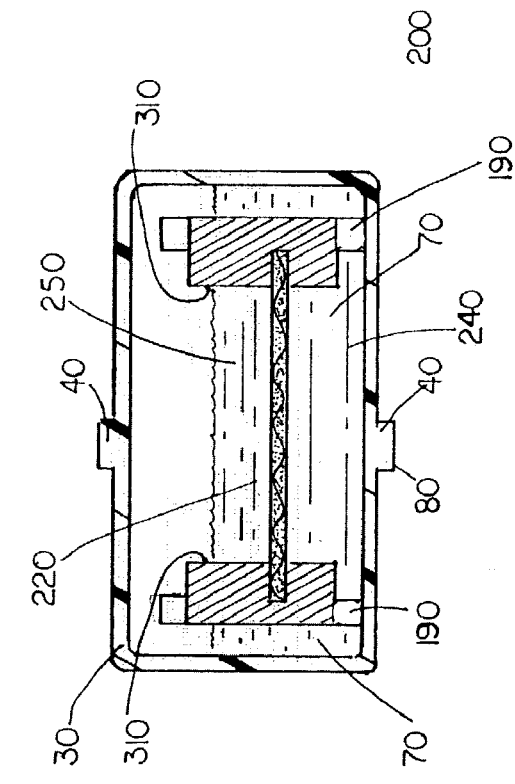
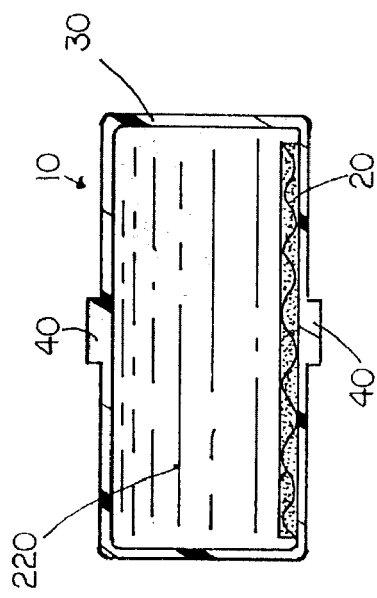
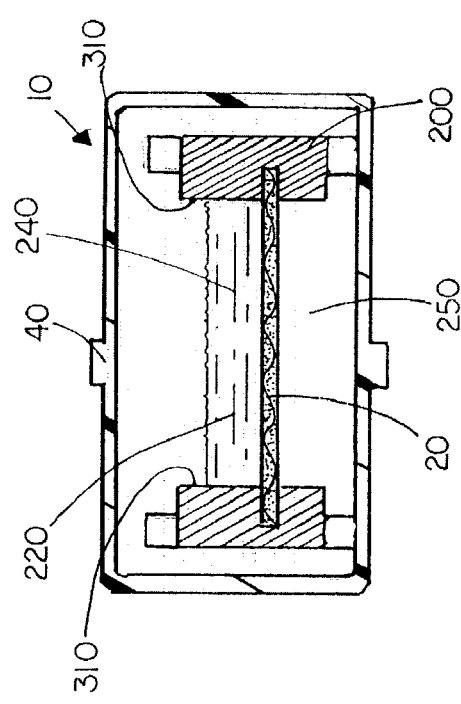
FIG. 23A  FIG. 23B  FIG. 23C
FIG. 24A  FIG. 24B

APPARATUS AND METHOD FOR CULTURING AND PRESERVING TISSUE CONSTRUCTS

RELATED APPLICATION

The present application claims the benefit of U.S. Provisional Application No. 60/388,567 filed Jun. 13, 2002, which is incorporated herein in its entirety by reference.

BACKGROUND OF THE INVENTION

1. Technical Field

The present invention relates to the culture, handling, preservation, storing, reconstitution, and shipping of cells and tissue. Specifically, the present invention relates to apparatus and methods for culturing and preserving cells and tissue in an enclosure without the need to remove them from the enclosure at any point during the sterilization, seeding, culturing, cryopreservation, shipping, or restoration process. Also disclosed is an apparatus and method of pipette interface with a container in a manner that blocks contaminants from entering the container.

2. Discussion of the Related Art

Tissue constructs hold promise to provide societal health care benefits. A wide variety of potentially beneficial applications are emerging, some with the potential to repair defects or abnormal tissues in the body, including those related to wound care, cardiovascular disease, and orthopedic care. These applications are anticipated to result in a tremendous amount of tissue constructs being produced annually to meet the needs of society. The tissue culture device used for tissue construct culture plays a critical role in the cost of production, which in turn impacts overall health care costs to society.

The petri dish has commonly been used to culture tissue constructs for research and production applications because of its simplicity. Unfortunately, the petri dish does not provide optimal culture conditions or allow efficient production. The petri dish is subject to contamination, automated handling is difficult, tissue constructs residing in a petri dish are prone to gradient exposure, tissue constructs must be physically handled during the manufacturing process, controlling the final shape of the tissue construct is difficult, and the petri dish is not suited to efficient process control and quality control.

Another problem of the petri dish is related to inoculation of cell attachment matrices that facilitate three-dimensional culture such as collagen. Unless the tissue construct is to be the same size and shape as the petri dish, cells generally must be placed directly onto the cell attachment matrix, and not deposited gravitationally as is the case with most cell culture devices, in order to prevent cells from coming to reside on the petri dish itself. Cells residing on surfaces other than the cell attachment matrix can negatively impact the culture. Thus, the inoculation procedure does not have tight process control since cells must be directed, usually manually, to specific locations on the cell attachment matrix. This problem is magnified as production is scaled up to produce more and more tissue constructs.

An example of a typical tissue construct culture process in a petri dish, the culture of skin, illustrates the problems. One method of culturing living skin in described by Eisenburg in U.S. Pat. No. 5,282,859. A cross-linked collagen sponge is created in a manner that renders it porous on one side and having a non-porous skin on the other side. Fibroblast cells are inoculated by "injecting" them onto the porous side of the collagen sponge, which resides in a petri dish. Culture medium is placed in the petri dish, which is incubated for 10 days while the fibroblasts proliferate. The culture medium is replaced every second day, requiring the device to be exposed to potential contamination on 5 separate occasions. It may be helpful to condition the medium by exposing it to keratinocytes for a 2-day period before use. Subsequently, the collagen sponge is turned over and the non-porous side is inoculated with keratinocytes by dispensing drops of inoculum onto various portions of the sponge. The sponge is then incubated with culture medium supplemented with fetal bovine serum for 10 days, again requiring the lid of the petri dish to be removed every other day for feeding.

In this example, the petri dish is subject to contamination due to the repeated handling needed for feeding. The delivery of cells also creates contamination risk. There is no way of controlling the amount of medium that resides on each side of the sponge because that is dictated by the density of the sponge relative to the density of the medium. When the sponge is denser that the medium, it sinks to the bottom of the petri dish. When the sponge is facing fibroblast side up, fibroblasts are exposed to the majority of medium in the petri dish. After keratinocyte inoculation, fibroblasts face the bottom of the petri dish exposing cells located towards the center of the sponge to different concentrations of medium substrates than those located towards the perimeter of the sponge, since the medium will form gradients towards the center of the sponge due to the metabolic activity of the cells. The proliferation of the cells is a function of how evenly distributed the cells are on the sponge. Therefore, outgrowth varies between each living skin construct produced in proportion to the variance in the inoculation process. If humans are depositing the cells by way of pipetting or syringe deliver, skin constructs will exhibit a high degree of variance in the initial distribution of cells, even when only one operator inoculates multiple sponges. More variance can be expected with multiple operators. Robotic dispensation reduces the variance, but increases complexity and does not diminish the exposure to contamination.

The petri dish is very poorly suited to protecting the collagen sponge or helping it retain its desired shape. The collagen sponge must be physically contacted to lift it and turn it over when the opposite side of the sponge is inoculated with keratinocytes. This risks damage to the sponge and fibroblasts and again exposes the sponge to contamination. When the culture proliferates, the sponge can contract, as collagen is known to do when cells grow upon and in it. Thus, the shape of the sponge can change and there is no control over the final shape, a particularly undesirable characteristic when creating skin constructs that may be laid side by side on a patient. This leads to an additional handling process to cut the sponge into a desired shape with all the risks of sponge damage and contamination present.

Long-term storage of the living skin cannot be done in the petri dish because the materials are not compatible with freezing. Therefore, the lid of the petri dish must again be removed and the sponge, now in a weakened condition after having been exposed to culture medium for 20 days, must be physically picked up and placed in a cryopreservation bag. Subsequently, the bag must be sealed and filled with cryopreservatives, the process again risking damage to the cells and sponge, and risking contamination. This also makes it difficult to perform quality control in a manner that is inexpensive. Even if non-destructive process control limits were met during the culture process, such as glucose and oxygen consumption targets, and those process control evaluations are not capable of detecting problems that occur once the culture is complete and the sponge is transferred to a cryopreservation bag. If damage or contamination occurs at that point, it will be expensive to detect because the skin will have to be quarantined or a high amount of destructive testing will be needed to verify the transfer procedures used for any given batch of skin were acceptable. Another potential problem in process control occurs because the amount of cryoprotectant on each side of the sponge is a function of where the sponge comes to reside in the cryopreservation bag, over which the operator has little control.

Reconstituting the skin after cryopreservation can be done by removing the skin from the cryoprotectant bag, placing it in a petri dish, and adding the appropriate medium to reconstitute it, thereby causing handling and contamination exposure. Subsequently, the sponge needs to be removed from the petri dish for use, or if not reconstituted at the site of use (i.e. the hospital), packaged in another bag for shipping. This example demonstrates that it is very difficult to establish tight process control for making tissue construct products using the petri dish and a new apparatus and method is needed.

Ideally, the apparatus and method would allow protocols that are established in the research stages to be relevant in the production stage. The simplicity of the petri dish is an advantage for those performing research scale cultures. Because the petri dish is compatible with typical equipment such as pipettes and incubators, and does not require perfusion, those options should remain available as the process is scaled up. In that manner, data generated at the research level would remain relevant as scale up occurs, and would not become irrelevant if the process were changed completely. Thus, once in the production scale, the device should be capable of operating with continuous perfusion or batch feeding. Gradient formation in the culture medium should be minimized in both batch fed and perfusion modes of operation. The improved device should have an inoculation process that is repeatable, such as the gravitational method commonly used to seed tissue culture flasks. Cells should come to reside upon the cell attachment matrix as opposed to other surfaces of the device. It should be also possible to control the final shape of the tissue construct in a manner that does not expose the construct to damage or contamination. Also, it is critical that the alternative does not repeatedly expose the tissue to contamination during the inoculation, feeding, cryopreservation, reconstitution, storage, or shipping stages. Since the possibility of exposing certain types of cells to medium containing conditioning agents may produce better tissue, as in the skin culture example of medium is conditioned by exposure to keratinocytes, the alternative device should contemplate attributes that may cost reduce this process. For example, the use of a membrane to place desired compounds and molecules in proximity of specific areas of the tissue may reduce cost by limiting the amount of those compounds and molecules needed in the device.

Attempts to address the limitations of the petri dish have been undertaken, but each attempt only addresses a portion of the problems and even when combined they do not lead to an alternative that has most of the desired attributes.

Bell, U.S. Pat. No. 4,435,102, describes a container housing a tissue for the purpose of assessing the interaction of the tissue and at least one agent. Although not directed towards overcoming the problems of tissue culture in petri dishes, the art is useful as it provides a method of controlling the amount of fluid residing above and below the tissue. This is advantageous relative to the inability of the petri dish to maintain predetermined volumes of culture medium above and below the construct. Additionally, Bell teaches a method for controlling the shrinkage of the tissue by either constraining the perimeter or allowing it to attach to a membrane for constraint. A method of constraining the controlling the shape of the tissue construct by constructing the collagen matrix in a frame of stainless steel mesh is also disclosed by Bell in U.S. Pat. No. 4,485,096.

Bell provides concepts that can be used to address some of the problems of tissue culture in petri dish. However, by applying them to the skin culture process described above, it can be seen that many problems remain. Bell does not make it clear how to minimize contamination potential throughout the inoculation, feeding, cryopreservation, reconstitution, and preservation stages. Proper oxygenation of the tissue, when cells occupy all sides of the cell attachment matrix, can only be achieved by perfusing the device with oxygenated medium. This is too complex and costly for most research environments. Unless the lower compartment is perfused with oxygen-saturated medium, cells in long-term culture will quickly deplete medium in the lower compartment of oxygen. Because of the low solubility of oxygen in medium relative to the solubility of needed substrates in medium like glucose, perfusion of the lower compartment to provide oxygen requires a much higher flow rate than if perfusion just provided substrates. That increases system complexity and cost and subjects cells to a higher rate of shear than may be desirable. If perfusion to bring oxygen is not provided once the oxygen in the lower compartment is depleted, the lower portion of the tissue can only obtain oxygen from the medium in the upper compartment. Since the cells on the upper portion of the tissue have first access to oxygen in the medium, the cells on the lower portion of the tissue are subject to oxygen concentrations that are always reduced relative to the cells on the upper portion of the tissue. Thus, without high flow perfusion, the device is no better than the petri dish for oxygenating cells at the bottom of the tissue.

In applications where the tissue is to be applied to a patient, such as living skin, Bell does not provide for a way of preparing the tissue without risking damage or increasing contamination risk. If the device were to be opened at a hospital for example, the tissue would have to be cut out of the frame constraining it. Therefore, since techniques of cutting the tissue are likely to vary from hospital to hospital, little process control is available. A controlled process would remove the tissue in the same manner each time and lead to superior and consistent overall tissue quality.

Kemp et al., U.S. Pat. No 5,536,656 describes controlling shrinkage by way of casting a collagen lattice on an acellular, hydrated collagen gel in contact with a permeable member. For some applications, this minimizes the need to constrain the collagen about the perimeter. The use of an absorbent member in the second, lower compartment in order to provide a consistent and level physical support for the collagen matrix is disclosed. Advantages are described whereby the absorbent member may create diffusional barriers to help retain desirable cell conditioning factors in proximity of the tissue. However, that same characteristic can limit transport of desired molecules and compounds to the tissue from the surrounding medium. Both the permeable membrane and the absorbent member can act to prevent inoculation of two sides of a cell attachment matrix because those members block cells from reaching the cell attachment matrix. Importantly, this is not a closed system and the risk of contamination is not diminished relative to the petri dish, and may actually be increased as two open compartments need to be manipulated. Furthermore, oxygenation of the culture is limited to diffusion of oxygen from the upper liquid/gas interface. The device does not lend itself to process control during scale up since it is not possible to measure the medium for indicators such as oxygen and glucose without taking individual samples from each device.

Peterson et al., U.S. Pat. No. 6,121,042, discloses an apparatus and method for seeding and culturing three-dimensional tissue constructs and creating a dynamic environment, placing mammalian cells under simulated in vivo conditions resulting in tissue that is more likely to display the biochemical, physical, and structural properties of native tissues than tissue cultured in a petri dish. The apparatus and methods utilize a variety of methods for physically moving the tissue. Magnetic axial loading and mechanical axial loading of the tissue by way of a piston, bellows, and flexible diaphragm, and pressure cycling the environment are described. The system is overly complex for tissue that is functionally adequate without being physically placed in tension. Thus, at the research scale, the complexity and cost are prohibitive and unnecessary for many applications. Even if the tissue loading elements are eliminated from the treatment chamber, the system is still too complex for research applications as it relies on pumps and other perfusion support mechanisms. It does not make it clear how to inoculate the tissue support matrix in a manner that achieves repeatable, uniform seeding of the type needed for applications like the production of living skin. It also does not allow removal of the construct from its constraints without risking contamination of the treatment chamber and does not indicate how to prevent damage to the construct during the removal process.

The focus is on ligaments, in which an improvement relative to the petri dish is attained due to the capability of physically stressing the ligament by altering it dimensionally. In this manner the ligament is cultured under conditions more representative of those found in vivo. However, whether or not the apparatus and method are applied to ligaments or some other tissue such as skin, many limitations of the petri dish remain. There is no ability to vary the cross-sectional area of fluid normal to the plane of the construct, remove trapped gas in a non-perfused system, alter the diffusional distance for gaseous communication with the tissue during culture, adequately oxygenate and feed the culture in the non-perfused state, direct cells to the appropriate location during seeding, make use of centrifugal force as a method of seeding a cell attachment matrix, control the final shape of tissue construct while retaining a closed system, allowing control of predetermined molecules and compounds present in proximity of the tissue. Furthermore, the apparatus and method does not contemplate the need to protect the bioreactor housing from damage during cryopreservation if the housing is comprised of a gas permeable material, capable of providing passive or non-passive gas transfer to and from the culture, but not entirely compatible with cryopreservation conditions. Also, the use of standard laboratory pipettes for liquid handling in a manner that minimizes contamination is not contemplated. The apparatus and methods are also complex and eliminate the most desirable attribute of the petri dish, which is its simplicity.

SUMMARY OF THE INVENTION

The present invention provides methods and apparatus for inoculating, culturing, cryopreserving, storing, reconstituting, and shipping tissue constructs in a simple manner that minimizes contamination risk.

One inventive aspect of the present invention involves the use of a flexible tissue construct bioreactor housing that can change shape without allowing contamination. The ability for the housing to change shape allows a variety of benefits to accrue. Changing the shape of the housing can be done to locate inoculum entirely over the target seeding area during gravitational seeding and allow the optimal amount of inoculum to reside above the cell attachment matrix during gravitational seeding and subsequently the housing volume can again change to accommodate the optimal medium volume residing in proximity of the tissue, alter the cross-sectional area so that the velocity of fluid in proximity of the tissue can be changed without altering the overall perfusion rate, relieve pressure increases that may result as medium loses its gas carrying capacity during a temperature increase when batch feeding is utilized, remove gas that comes to reside in the bioreactor without having to displace it with medium and potentially dilute important cell produced conditioning agents, change the volume of space surrounding the tissue in order to accommodate the addition of the optimal amount of cyropreservative, change in volume of space surrounding the tissue in order to accommodate the addition of the optimal amount of reconstitution medium, drive an internal die through the construct to cut it to a desired shape, or allow microscopic viewing of the tissue.

When the housing of the bioreactor is gas permeable in addition to being flexible, moving the gas permeable housing closer or farther away from the tissue construct will allow oxygen tension to be altered at the cell location. In this manner, altering oxygen tension can be done independent of the ambient surroundings, substantially simplification relative to other tissue construct devices. Another unique advantage can be obtained if the moisture vapor transmission rate differs across separate surfaces of the bioreactor housing. This allows more resolution in controlling the osmotic conditions in proximity of the cells due to evaporation. This is particularly beneficial in a batch fed process, where there is no replacement of medium for fixed intervals of time.

Another inventive aspect of the present invention is the ability to inoculate and culture cells on a cell attachment matrix residing within a flexible housing in a batch fed manner that retains the simplicity of the petri dish, but is superior in terms of minimizing contamination risk, improving inoculation distribution, reducing gradient formation, and controlling oxygen tension. The tissue construct resides upon a support matrix that places it in a position that allows a desired volume of fluid to reside around it. Also, resolution in oxygen tension control is available by moving the gas permeable walls closer or farther away from the cells while retaining the same amount of medium in the bioreactor, thereby leaving the concentration of important cell secreted conditioning factors unaltered.

Another inventive aspect of the present invention is the ability to compartmentalize the bioreactor. This has benefits including allowing each side of a tissue or cell attachment matrix to be subjected to a different medium conditions, allowing inoculation of different cell types onto different surfaces, and exposing different areas of the cell attachment matrix to different growth conditions such as different oxygen tension or different glucose concentrations.

Another inventive aspect of the present invention is the ability to allow cells of a different type be co-cultured, physically separated by a semi-permeable membrane, in a manner that includes the attributes of improved oxygen tension control, better seeding distribution during inoculation, and reduced gradient formation.

Another inventive aspect of the present invention is the ability to cut the tissue to a desired shape without need to expose the tissue to contamination by opening the bioreactor.

Another inventive aspect of the present invention is the ability to inoculate one or two sides of a cell attachment matrix by intermittently positioning the bioreactor in a vertical and horizontal position in order to allow a well mixed inoculum to deposit cells in a well distributed pattern upon a cell attachment matrix, and create optimal culture conditions by allowing the tissue to receive medium in perfusion or batch modes.

Another inventive aspect of the present invention is the ability to seed cells into a cell attachment matrix by the use of centrifugal force.

Another inventive aspect of the present invention is the ability to access a septum by way of a needle while protecting both the needle and septum from exposure to contamination before, during, and after needle penetration.

Another inventive aspect of the present invention is the ability to access a flexible container with a pipette in a manner that prevents contaminants from entering the container while the pipette is engaged in the access port of the container.

It is yet another inventive aspect of the present invention to enclose the tissue construct bioreactor in a package that prevents damage to the tissue during cryopreservation even if the housing to the bioreactor is damaged during the process.

BRIEF DESCRIPTION OF THE DRAWINGS

FIG. 1 is an embodiment of a tissue construct bioreactor housing a cell attachment matrix.

FIG. 2A, FIG. 2B, and FIG. 2C disclose an example of an embodiment in which the tissue construct bioreactor is configured to be shipped, sterilized, and stored in a minimum volume condition, expand in volume at the onset of the culture process, and change in volume during the culture process.

FIG. 3A and FIG. 3B disclose an example of an embodiment of this invention in which the walls of the tissue construct bioreactor are comprised of a rigid material. The tissue construct bioreactor is configured to change in volume during the culture process without breaching sterility.

FIG. 4A and FIG. 4B disclose a configuration of an embodiment where gas is removed from tissue construct bioreactor without displacing it with liquid.

FIG. 5A, FIG. 5B, FIG. 5C, and FIG. 5D show an embodiment of a tissue construct bioreactor configured to allow cells to be seeded onto one side of the cell attachment matrix, and subsequently allow a desired amount of medium to reside on each side of the cell attachment matrix by positioning the tissue construct bioreactor in a vertical position.

FIG. 6A and FIG. 6B show an embodiment for inoculating both sides of a cell attachment matrix and allowing a predetermined amount of medium to reside on each side of the cell attachment matrix.

FIG. 13A and FIG. 13B show one example of an embodiment of a tissue construct bioreactor comprising two compartments and a cutting die useful for separating the desired portion of the cell attachment matrix from the undesired portion.

FIG. 14A and FIG. 14B show cross-sectional views of an embodiment in which a tissue construct bioreactor is configured to allow a cell attachment matrix to be removed.

FIG. 15A and FIG. 15B show the inoculation and feeding stages of an embodiment of a tissue construct bioreactor in which a cell attachment matrix is held in a desired position by a frame.

In FIG. 16, a non-flexible outer housing mates with a flexible tissue construct bioreactor wall at predetermined points to prevent it from collapsing.

FIG. 23A, FIG. 23B, and FIG. 23C shows a gravitational method of inoculating two sides of a cell attachment matrix residing within a compartmentalized tissue construct bioreactor.

FIG. 24A and FIG. 24B show an embodiment for inoculating one side, and feeding both sides, of a cell attachment matrix.

Figure 7:
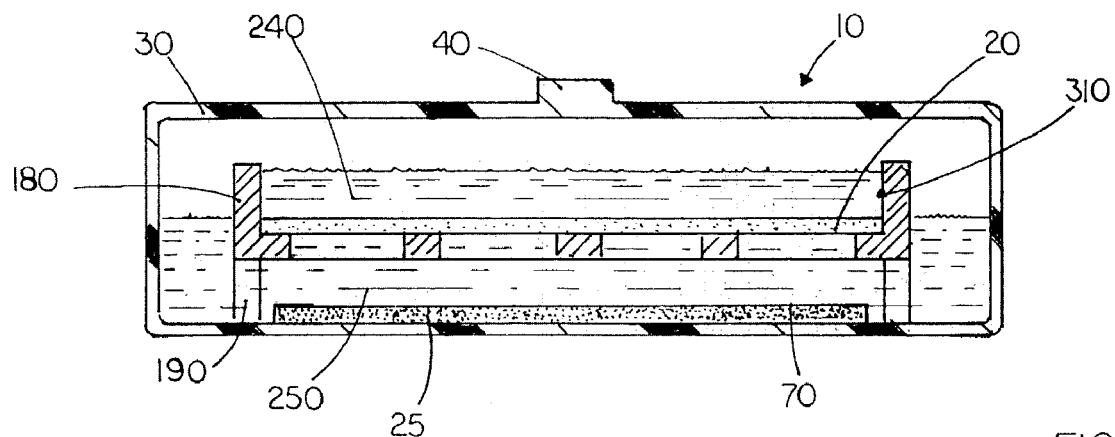
FIG. 7 shows one embodiment of a tissue construct bioreactor that allows a desired amount of medium or fluid to reside on each side of a cell attachment matrix.

REFERENCE NUMERALS IN DRAWINGS 10 tissue construct bioreactor
20 cell attachment matrix
25 lower cell attachment matrix
30 tissue construct bioreactor walls
35 wall seal
37 clamp
38 constraining clamp
40 access port
42 thin walled access opening
43 pipette tip
44 pipette
45 void volume
46 fluid access channel
47 pipette stop
48 threads
49 flexible tube
51 cap
60 gas
70 cell culture medium
80 septum
90 syringe needle
100 syringe
110 syringe flow direction
120 wall direction arrow
130 cryopreservation enclosure
140 gas compartment
145 gas compartment access port
150 sterile gas filter
160 gas compartment spacer
170 cutting die
180 matrix holder
190 legs
200 frame
202 membrane
220 inoculum
230 compartmentalized tissue construct bioreactor
240 first compartment
250 second compartment
260 bioreactor lid
270 bioreactor body
280 lid seal
290 moveable latch
310 vertical walls
330 outer housing
340 boss
350 pocket
360 spacer projections
370 grid
380 access needles
390 access needle protection septum

DETAILED DESCRIPTION OF THE INVENTION

The following embodiments of the present invention will be described in the context of an apparatus and method for seeding a cell attachment matrix with tissue, culturing, preserving, reconstituting, altering the geometric shape of, shipping, and removing the tissue. Those skilled in the art will recognize that the apparatus and methods are useful for broader applications including those in which tissue is present without a cell attachment matrix.

FIG. 1 shows an embodiment of a tissue construct bioreactor 10 configured for culture of a tissue construct. Cell attachment matrix 20 resides within tissue construct bioreactor 10 for the purpose of becoming populated with cells of a desired type. Tissue construct bioreactor walls 30 are liquid impermeable, and closed to the ambient gas. Cell attachment matrix 20 can be any material capable of allowing cells to reside upon it, or within it. For example, it can be comprised of collagen gel [Yang et al., 1981] cellulose sponge [Leighton et al., 1951], collagen coated cellulose sponge [Leighton et al., 1968], gelatin sponge, Gelfoam™ [Sorour et al., 1975], collagen sponge cross-linked to form one side into a non-porous skin [Eisenburg 2000], porous polyvinyl formal resin [Tun et al. 2000], nylon, dacron, polystyrene, polypropylene, polyacrylates, polyvinyl compounds, polycarbonate, polytetrabluoroethylene, thermanox, nitrocellulose [Naughton et al., 1999], microporous membrane, semipermeable membrane, or any other material that has been used for tissue culture. Preferably, cell attachment matrix 20 resides within tissue construct bioreactor 10 prior to sterilization. That minimizes contamination risk associated with aseptic insertion. However, depending on the characteristics of cell attachment matrix 20, such as compatibility with various sterilization methods, aseptic insertion may need to occur after tissue construct bioreactor 10 has been sterilized or it may be formed in place.

If at least a portion of one tissue construct bioreactor wall 30 is a comprised of a liquid impermeable, gas permeable material, gas can diffuse into and out of tissue construct bioreactor 10. That allows cells to obtain gas exchange independent of the rate of cell culture medium delivery. In many perfused bioreactors, medium is oxygenated prior to delivery to the bioreactor. The low solubility of oxygen in medium, when compared to substrates such as glucose and essential amino acids, requires perfusion rates be dictated by the oxygen demand of the tissue construct. However, by making a portion of the bioreactor housing gas permeable, perfusion of oxygenated medium into the bioreactor to support cellular demand can be avoided. When oxygen is delivered by way of the gas permeable bioreactor housing, several factors affect the delivery rate of oxygen to the cell mass. They include the surface area of gas permeable material available for transfer, permeability of the gas permeable material, the degree of parallelism between cell attachment matrix 20 and gas permeable tissue construct wall 30, the distance between gas permeable tissue construct wall 30 and the cell mass, and if gas and liquid resides in tissue construct bioreactor 10, the distance between the cell mass and the gas/liquid interface.

The amount of cell culture medium residing in gas permeable tissue construct bioreactor 10 has an effect on bioreactor geometry and gas exchange. If cell culture medium is delivered in a batch fed mode, the geometry of tissue construct bioreactor 10 should take into consideration the need to provide the tissue construct with enough cell culture medium to sustain the culture for a predetermined period of time. When feeding is done manually, typically at least 24 hours between cell culture medium exchanges is most convenient for operators. Additional cell culture medium capacity will make feeding less frequent, but should be balanced against any negative impact on gas exchange if the distance between the cell mass and the oxygen source increases as a result of increasing cell culture medium capacity.

Since petri dish culture of tissue constructs is common, the petri dish geometry provides a good reference for batch fed tissue construct bioreactor design. Typically, in petri dish culture, the tissue construct not the same dimension as the petri dish and therefore not all of the cell culture medium resides directly above the tissue construct. Thus, the distance from the tissue construct to the gas/liquid interface is less than it would be if all of the liquid resided directly above the tissue construct. As a result, when the volume of medium is fixed, oxygen is required to travel farther and surface area for gas transfer is reduced as the configuration is altered to allow more medium to reside directly above the tissue construct. For example, if a 6 cm×6 cm cell attachment matrix resides in a 145 mm diameter petri dish (165 cm$^2$ surface area) containing 50 ml of cell culture medium, the height of liquid that resides in the petri dish is approximately 3.0 mm. However, if the bottom of the petri dish were the same size and shape as the cell attachment matrix, thereby allowing liquid to reside entirely over the cell attachment matrix, the height of liquid above the cell attachment matrix would more than double to 7.2 mm.

Despite increasing the distance from cells to the gas source and limiting the surface area available for gas transfer, there are advantages to configurations in which a majority of the cell culture medium resides above the tissue construct. For example, during gravitational seeding if inoculum resides directly over the cell attachment matrix cells will deposit upon the cell attachment matrix, and not upon other areas of the bioreactor as commonly occurs with petri dish culture. Minimizing the amount of cell attachment onto areas of the bioreactor other than the cell attachment matrix is useful for applications in which cells that deposit and attach to surfaces of the tissue construct bioreactor, other that the cell attachment matrix, have a detrimental effect on the culture as described in U.S. Pat. No. 5,266,480. For applications that are typically performed in petri dishes, the tissue construct bioreactor can be configured to allow nearly all of the inoculum to reside directly over the cell attachment matrix.

In the case where the tissue construct bioreactor walls are not gas permeable, and perfusion is not present, configuring the tissue construct bioreactor so that it can contain a gas/liquid interface will allow gas exchange in a batch fed tissue construct bioreactor. The gas should be in sterile communication with a source of gas residing outside of the bioreactor. Gaseous communication by way of a gas permeable sterile filter will prevent contamination. The gas/liquid interface acts to increase surface area for gas transfer relative to a non-gas permeable tissue construct bioreactor completely filled with cell culture medium.

If gas permeable walls are desired, a variety of gas permeable materials can be used. In general, suitable gas permeable materials are flexible. If the tissue construct bioreactor is comprised of flexible materials, there can be geometric benefits in addition to gas exchange as described herein. The best choice of material for gas exchange depends on the specific culture application. As a general guideline, the gas permeability of a given material should be considered in addition to the interaction of the material with either cells or protein structures. Liquid impermeable films of an equivalent thickness, exposed to equivalent cellular oxygen demand, will establish various steady state oxygen tensions in the cell culture medium. For example, fluorinated ethylene polymers, silicone, Teflon, and silicone polycarbonate copolymers will establish higher oxygen tension in the tissue construct bioreactor than will polyethylene, polycarbonate, polypropylene, polysulfone, or polypropylene polymers. In some cases, such as when cost can be reduced or a hard shell housing can make handling easier, it may be desirable to only have a portion of the tissue construct bioreactor gas permeable. This is acceptable, provided that adequate gas exchange is achieved. In other cases, it may be desirable to have more than one type of gas permeable material present, such as the case where different gas transfer rates are desired. For example, when both the upper and lower tissue construct bioreactor walls are gas permeable, it may be desirable to minimize evaporation at the location closet to the cell mass due to the potential for increased local osmolarity. If that were the case in the configuration described in FIG. 1, lower tissue construct bioreactor wall 30 could be a material with a lower moisture vapor transmission rate than the material selected for the upper tissue construct bioreactor wall 30.

Constructing the tissue construct bioreactor so that is can change volume without a breach in sterility can be beneficial. Benefits related to altering the volume of the tissue construct bioreactor include the ability to reduce the amount of packaging material, cost of transportation, and the use of inventory space. For example, packaging material can be reduced if the tissue construct bioreactor initially resides in a minimum volume state when place into a sterility bag, is subsequently removed from the sterility bag for use, and then expands in volume in response to fluids added during the cell culture process. The smaller sized sterility bag reduces the cost of packaging material, shipping, sterilization, and storage.

Furthermore, constructing the tissue construct bioreactor with the ability to change volume while remaining a closed system allows variability in the volume of gas and/or liquid that can reside in the tissue construct bioreactor at any given time. A wide variety of combinations of gas and liquid volumes can be retained in the tissue construct bioreactor.

Altering the distance between the tissue construct and the walls of the tissue construct bioreactor at some point after the culture process has been initiated can be beneficial. For example, bringing a wall of the bioreactor closer to the tissue construct at some point during a perfused culture may helpful in generating a well-mixed flow profile or altered velocity profile. Other beneficial reasons may be present, such as when the optimal volume of inoculum differs from the optimal volume of cell culture medium contained in the tissue construct bioreactor during the culture phase, when an increase in the gas exchange demands of a culture requires a gas permeable wall to get closer to the culture, when the oxygen tension that is optimal for cells needs to be altered without the ability to change the oxygen tension of the ambient surrounding, when microscopic viewing is needed and the focal length of the microscope at the desired magnification requires moving either the upper wall or lower wall closer to the tissue construct depending on what surface of the tissue construct is to be viewed, or when the appropriate volume of cryoprotectant differs from the appropriate amount of medium for culture.

FIG. 2A and FIG. 2B disclose an example of an embodiment in which tissue construct bioreactor 10 is configured to be shipped, sterilized, and stored in a minimum volume condition, expand in volume at the onset of the culture process, and change in volume during the culture process. To attain these objectives, at least one wall of tissue construct bioreactor 10 is flexible. FIG. 2A shows tissue construct bioreactor 10 in a state of minimum volume prior to the onset of the culture process. FIG. 2B shows tissue construct bioreactor 10 in a state of maximum volume, having been altered in volume as flexible tissue construct bioreactor wall 30 expands due to the addition of inoculum 220. FIG. 2C shows tissue construct bioreactor 10 in a state of reduced volume relative to that shown in FIG. 2B such as may be the case when the optimal volume of cell culture medium 70 is less than the volume of inoculum 220. Access into tissue construct bioreactor 10 can be made through a single access port 40. In this embodiment, tissue construct bioreactor walls 30 are comprised of flexible materials. Inoculum 220 can be delivered in a sterile manner by penetrating access port 40 with a needle, thereby causing tissue construct bioreactor 10 to expand in volume. Likewise, after cells of inoculum 220 have deposited onto cell attachment matrix 20, residual inoculum can be removed by a needle, thereby causing tissue construct bioreactor 10 to contract in volume.

The volume of the tissue construct bioreactor can be altered in a sterile manner without the use of flexible walls. FIG. 3A and FIG. 3B disclose an example of an embodiment of this invention in which tissue construct bioreactor 10 changes volume during the culture process. In this configuration, the walls of tissue construct bioreactor 10 are comprised of rigid materials. The upper tissue construct bioreactor wall 30 can be moved either towards or away from cell attachment matrix 20 at some predetermined point in the culture. Wall seal 35 between the upper tissue construct bioreactor wall 30 and the lower tissue construct bioreactor wall 30 prevents contamination or leakage. When reducing volume, such as when displacing inoculum 220 with cell culture medium 70 post cell attachment to cell attachment matrix 20, fluid can be displaced in a sterile manner into a liquid handling device such as syringe 100, or into a reservoir when perfusion is employed.

Minimizing the volume of gas residing within the tissue construct bioreactor can be beneficial in tissue construct applications in which cells should not come into direct contact with gas/liquid interfaces due to resulting detrimental effects such as those related to shear, or when cells, such as keratinocytes, can differentiate when exposed to gas. In bioreactors with a fixed volume, unwanted gas can become present during the culture even if it is not present at the onset of the culture. For example, this can occur if the cell culture medium rises in temperature, thereby experiencing a reduction in its gas carrying capacity. FIG. 4A and FIG. 4B disclose a configuration of an embodiment where gas 60 is removed from tissue construct bioreactor 10 without displacing it with liquid. Tissue construct bioreactor 10, which is configured to change in volume, retains only the initial volume of cell culture medium 70 after gas 60 is removed. Septum 80 is penetrated by syringe needle 90. The beginning of the process is shown in FIG. 4A, where syringe 100 is shown drawing gas 60 in the direction indicated by syringe flow direction arrow 110. Flexible tissue construct bioreactor wall 30 begins to move in the direction shown by wall direction arrow 120 as gas 60 is removed due to the pressure differential created across flexible tissue construct bioreactor wall 30. In FIG. 4B flexible tissue construct bioreactor wall 30 has collapsed to occupy the space in which gas 60 previously resided. If tissue construct bioreactor 10 could not change volume, and a single access port were desired, cell culture medium would have to be added to displace the gas. Thus both gas and cell culture medium would need to move simultaneously through the single access port, leaving the port open to contamination during this procedure. In a fixed volume tissue construct bioreactor, the use of two ports adapted for hermetic interface with liquid handling equipment, such as by the use of luer tapers, would minimize contamination. However, the need to add liquid in order to displace gas would change the quantity and perhaps the concentration of important metabolites.

Even in applications in which the presence of gas is acceptable from a biological standpoint, detrimental operational effects can occur if gas volume increases during use. A pressure increase within a bioreactor can occur when cell culture medium loses its gas carrying capacity if the tissue construct bioreactor is not free to expand in volume. Pressure will then seek to equilibrate with ambient conditions when the bioreactor access port, or ports, are accessed. This will increase the contamination risk if pressurized fluids, such as cell culture medium, are displaced from the bioreactor when a port is accessed. A flexible tissue construct bioreactor wall will alleviate this condition since it can expand to accommodate gas exiting the cell culture medium, thereby reducing the internal pressure relative to a bioreactor with non-flexible walls. Eventually, the gas permeable portion of the tissue construct bioreactor will allow pressure to equilibrate with ambient conditions by diffusion.

In a typical petri dish culture, the cell attachment matrix will settle to a given location determined by its specific gravity, and the amount of cell culture medium that resides on each side of the tissue construct is determined the location at which the cell attachment matrix comes to reside. Increasing control over the volume of medium residing on each side of the tissue construct can enhance repeatability in the culture process. The use of flexible tissue construct bioreactor walls can be advantageous when configuring the tissue construct bioreactor with the capability to allow a desired amount of cell culture medium to reside on each side of the tissue construct.

FIG. 5 shows an embodiment of a tissue construct bioreactor configured to allow cells to be seeded onto one side of the cell attachment matrix, and subsequently allow a desired amount of medium to reside on each side of the cell attachment matrix by positioning the tissue construct bioreactor in a vertical position. Cell attachment matrix 20 is captured on one edge by clamp 37, which is secured to tissue construct bioreactor 10. In FIG. 5A, tissue construct bioreactor 10 is positioned horizontally for gravitationally seeding cell attachment matrix 20. Cell attachment matrix 20 resides in proximity of the lower interior surface of tissue construct bioreactor wall 30 due to its specific gravity. If necessary, a weight can be attached to cell attachment matrix 20 to allow it to reach this lower surface by gravitational force. The weight should be positioned in a manner that maximizes the available surface for cell deposit onto cell attachment matrix 20. When cell attachment matrix 20 resides in proximity to the lower surface, the amount of inoculum that can reside between cell attachment matrix 20 and the lower interior surface is minimized, thereby maximizing cell deposit on cell attachment matrix 20. When minimizing the amount of cells that attach to surfaces other than cell attachment matrix 20 is desired, structuring the walls of tissue construct bioreactor 10 with hydrophobic materials is beneficial. Constraining clamp 38 limits the location of inoculum 220 such that the vast majority of inoculum 220 resides above cell attachment matrix 20 and cells settle onto the exposed face of cell attachment matrix 20. Alternatively, dimensioning the wall of tissue construct bioreactor 10 such that the vast majority of inoculum 220 resides above cell attachment matrix 20 will help direct cells to the surface of cell attachment matrix 20, as best shown in FIG. 5B.

The tissue construct bioreactor and inoculation process should typically be designed with the objective of achieving a relatively even distribution of cells across the desired surface of the cell attachment matrix, while minimizing the deposit of cells onto other surfaces. Thus, positioning the cell attachment matrix to reside in a planar state will enhance seeding uniformity. When the tissue construct bioreactor is in the horizontal position, a well mixed cell suspension placed above the cell attachment matrix will allow cells to gravitationally settle upon the matrix in a well distributed pattern. In some applications, it may be desirable for the contact force that cells make with the cell attachment matrix during inoculation to exceed that caused by gravity in order to drive them into cell attachment matrix 20. In that case, placing the mixed suspension in the tissue construct bioreactor, and then centrifuging the bioreactor in a direction and at a velocity that drives cells into the cell attachment matrix can achieve that purpose. The same accelerated force typically used to re-suspend the specific type of cells in the application should be the initial target force for seeding so that the cells remain undamaged. Proper physical support for cell attachment matrix 20 should be present so that it remains in a relatively planar state. Iterations to the rotation rate to achieve the most desirable seeding pattern may be necessary, depending on the specific combinations of materials, cell type, and desired degree of penetration.

After cells have attached to cell attachment matrix 20, tissue construct bioreactor 10 is oriented in a vertical position such that clamp 37 resides at the upper position as shown in FIG. 5C. To minimize gradient formation, flexible tissue construct bioreactor walls 30 are constrained by outer housing 330 such that they are substantially parallel to cell attachment matrix 20. For best control over the volume of medium that resides on each side of cell attachment matrix 20, cell attachment matrix 20 hangs in a relatively planar state under the force of its own weight, or an attached weight if necessary. The volume of cell culture medium 70 residing on either side of cell attachment matrix 20 can be controlled by orienting the constrained edge of cell attachment matrix 20 in a manner that positions it a desired distance from tissue construct bioreactor walls 30. For example, in FIG. 5C the distance between the each surface of cell attachment matrix 20 and tissue construct bioreactor wall 30 is relatively equal. In FIG. 5D, the constrained edge of cell attachment matrix 20 has been shifted towards the leftmost wall of outer housing 330 by rotating the perimeter of tissue construct bioreactor 10 in a counter clockwise direction. Post rotation, the volume of cell culture medium 70 residing to the left of cell attachment matrix 20 is less than that residing to the right of cell attachment matrix 20. Creating a non-symmetric position may be useful for a variety of reasons such as when only one of tissue construct bioreactor walls 30 is gas permeable and positioning one face of cell attachment matrix 20 closer to that gas permeable tissue construct bioreactor wall 30 enhances gas exchange of the cells residing on that face.

Rotating the perimeter of tissue construct bioreactor 10 is made possible due to the flexible material comprising tissue construct bioreactor walls 30. A portion of tissue construct bioreactor wall 30 can be comprised of rigid material, provided that the rigid portion does not preclude positioning cell attachment matrix 20 in the desired location. At a minimum, the perimeter section comprising the upper and lower portion of the tissue construct bioreactor walls, when oriented in the vertical position, should be flexible so that the cell attachment matrix is capable of moving into the desired location within the tissue construct bioreactor.

FIG. 6 shows a tissue construct bioreactor embodiment for inoculating both sides of the cell attachment matrix and allowing a predetermined amount of medium to reside on each side of the cell attachment matrix. Cell attachment matrix 20 is captured on one edge by clamp 37, which is secured to a flexible tissue construct bioreactor wall 30 section of tissue construct bioreactor 10. Those skilled in the art will recognize that any method used to secure one edge of cell attachment matrix 20 is acceptable. In FIG. 6A, tissue construct bioreactor 10 resides in a horizontal position such that inoculum 220 gravitationally seeds onto the uppermost face of cell attachment matrix 20, which resides in proximity of the lower interior surface of tissue construct bioreactor 10 due to its specific gravity. If necessary, cell attachment matrix 20 can be weighted to allow it to reach this lower interior surface by gravitational force. The weight should be positioned in a manner that maximizes the available surface for cell deposit onto cell attachment matrix 20. Residing in proximity to the lower surface minimizes the amount of inoculum that can reside between cell attachment matrix 20 and the lower interior surface, thereby maximizing cell deposit onto the trapped upper face of cell attachment matrix 20. After cells have attached to cell attachment matrix 20, tissue construct bioreactor 10 is turned over and clamp 37 is positioned such that cell attachment matrix 20 is in proximity of the lower interior surface of tissue construct bioreactor 10 as best shown in FIG. 6B. Inoculum 220 containing the type of cells desired is placed into tissue construct bioreactor 10, preferably such that the vast majority of it resides above cell attachment matrix 20. Cells settle by gravity, or alternatively by centrifugation, onto the exposed surface of cell attachment matrix 20. After cells have attached to cell attachment matrix 20, tissue construct bioreactor 10 is oriented in a vertical position such that clamp 37 resides at the upper position as previously described and shown in FIG. 5B. Adjusting the volume of cell culture medium residing on each side of the cell attachment matrix can be accomplished as previously described and shown in FIG. 5C.

FIG. 7 shows another embodiment a compartmentalized tissue construct bioreactor 230 that allows a desired amount of medium or fluid to reside on each side of cell attachment matrix 20. Matrix holder 180 holds cell attachment matrix 20 in a desired location. In this configuration, a predetermined volume of cell culture medium 70 resides below cell attachment matrix 20 in second compartment 250. Matrix holder 180 has legs 190 dimensioned in height to allow the predetermined volume of cell culture medium 70 to reside below cell attachment matrix 20. Matrix holder 180 should be designed with consideration given to the mechanical strength of cell attachment matrix 20 when wet. If cell attachment matrix 20 is not capable of supporting its own weight, matrix holder 180 makes contact with the lower surface of cell attachment matrix 20. Matrix holder 180 can be comprised of a variety of materials and configurations that allow cell culture medium 70, or desired compounds of cell culture medium 70, to contact cell attachment matrix 20. Support configurations include microporous membranes, semi-permeable membranes, support grids, and open weave mesh. Unless membranes are used for support, matrix holder 180 should be configured such that minimal contact with cell attachment matrix 20 exists, thereby permitting relatively unencumbered delivery of nutrients and removal of waste products. For example, an open diamond weave mesh such as that with ½ inch openings (Catalogue # 18-157-50 Nalle Plastics, Austin Tex.) is capable of providing adequate structural support and allowing relatively unencumbered mass transfer when cell attachment matrix 20 is comprised of 0.020 inch thick bovine collagen. If microporous or semipermeable membranes are used, additional physical support structures may or may not be needed depending on the capacity of the membrane to retain cell attachment matrix 20 in a relatively planar state. For example, cellulose membranes swell when wet. When sealed around their perimeter in the dry state, and then wetted, the swelling causes slack in the membrane thereby reducing its capacity to maintain a planar position. However other membranes, such as microporous polycarbonate membranes, retain dimensional stability when wetted. If the purpose of using membranes is to make compounds and molecules of a predetermined size available to the tissue construct by physically preventing undesired compounds and molecules of a predetermined size from moving from the cell culture medium residing in first compartment 240 with that residing in second compartment 250, the perimeter of the membrane must seal to matrix holder 180 to prevent shunting of undesired compounds and molecules. In the preferred embodiment, cell attachment matrix 20 resides in a substantially horizontal position such that cells can settle onto the entire surface of cell attachment matrix 20 during inoculation. Matrix holder vertical walls 310 retain inoculum 220 above cell attachment matrix 20 in first compartment 240 during seeding. When tissue construct bioreactor 10 resides in the horizontal position, and the density of cell attachment matrix 20 exceeds that of cell culture medium, and cell attachment matrix 20 is not physically constrained, gravity keeps cell attachment matrix 20 located upon matrix holder 180. Gas that may become present directly below cell attachment matrix 20 will act to inhibit mass transfer of solutes. Any gas that becomes trapped below cell attachment matrix 20 can be removed by orienting tissue construct bioreactor 10 in a manner such that gas is allowed to rise from under cell attachment matrix 20 without permanently dislodging cell attachment matrix 20 from matrix holder 180. If cell attachment matrix 20 is physically constrained to maintain its position upon matrix holder 180, care should be taken to ensure the mechanism acting to constrain cell attachment matrix 20 does not inhibit uniform seeding, feeding, or gas exchange.

For co-culture applications in which it is desirable to separate cells, two cell attachment matrices can reside in the bioreactor. FIG. 7 shows optional lower cell attachment matrix 25, useful for co-culture. When matrix holder 180 integrates a membrane in the manner described above, the membrane can be used to retain desirable molecules and compounds in the presence of cells on one cell attachment matrix without allowing those molecules and compounds to be available to cells of the other cell attachment matrix. In some cases it may only be desirable to prevent cells from migrating from one cell attachment matrix and making physical contact with cells of the other cell attachment matrix. Thus, the particular purpose of the co-culture application will dictate the molecular weight cutoff or microporosity of the membrane. As one example, in co-culture applications typically performed in commercially available devices, such as a transwell, microporous membrane with a 0.2 to 1.2 micron opening is preferred. In other applications, a lower cutoff may be desirable such as a 10,000 MWCO non-protein binding membrane when serum is in proximity of one cell attachment matrix but not in the other. The type of membrane best suited for a given application will be based upon many variables including size exclusion, cell attachment capacity, protein binding characteristics, sterilization compatibility, mass transfer capacity, cost, commercial availability, and biocompatibility. Those not familiar with the best choices for the membrane properties should review literature describing the use of membranes in cell culture applications. It should also be noted that the use of the description cell attachment matrix does not preclude the use of suspension cells. Additionally, the cell attachment matrix may be the membrane and the lower wall of the tissue construct bioreactor or just the upper and lower sides of the membrane. For example, a commonly used material for cell culture is polystryene, which if present in the lower tissue construct bioreactor wall 30 would allow the wall to constitute a cell attachment matrix for adherent cells to attach to or suspension cells to reside upon. However, for suspension cells there may be an advantage when the lower tissue construct wall is comprised of gas permeable material, thereby allowing better gas transfer of the suspension culture than if the oxygen were delivered by way of a gas liquid interface above the cells. In this case, for definition purposes, the lower tissue construct wall would also constitute a cell attachment matrix. A main advantage that the tissue construct bioreactor brings to co-culture relative to the traditional use of a transwell is the capacity to remain a closed system and place cells of the lower cell attachment matrix 25 in closer proximity of gas exchange when the lower tissue construct bioreactor wall is comprised of a gas permeable material.

Figure 8:
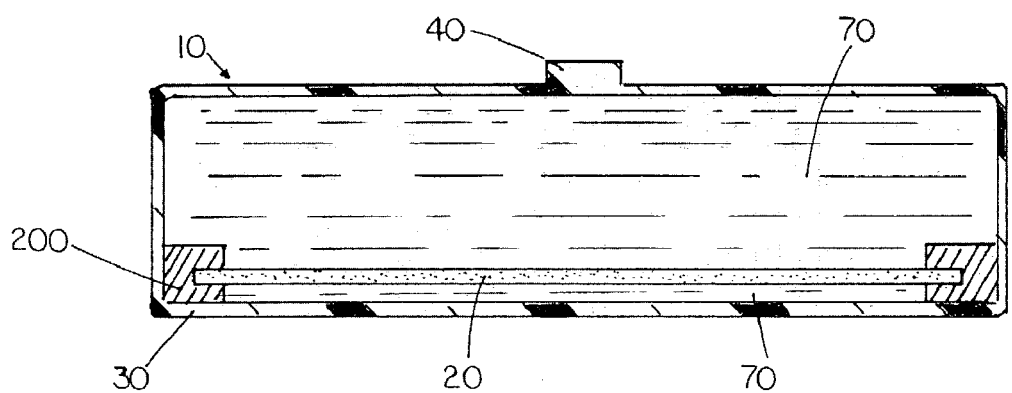
FIG. 8 shows an embodiment of a tissue construct bioreactor in which a cell attachment matrix is held in a desired position by a frame.

FIG. 8 shows an embodiment of tissue construct bioreactor 10 in which cell attachment matrix 20 is held in a desired position by frame 200. In this configuration, frame 200 is configured to allow a defined volume of cell culture medium 70 to reside below cell attachment matrix 20 and to prevent cell attachment matrix 20 from changing shape during the culture process. The lower surface of cell attachment matrix 20 has unobstructed contact with cell culture medium 70 when frame 200 is designed to allow medium to move through it. Unobstructed contact with medium 70 can also be attained using the materials and methods described for matrix holder 180 of FIG. 7. If cell culture medium 70 is added to tissue construct bioreactor 10 while tissue construct bioreactor 10 resides in a horizontal position, the design should allow gas to exit from the volume of space directly below cell attachment matrix 20. This can be achieved by a method of adding cell culture medium 70 until its height exceeds the height of the lower surface of cell attachment matrix 20, and temporarily orienting tissue construct bioreactor 10 to a position that allows gas to move away from the lower surface of cell attachment matrix 20. Another method would be to add the medium while tissue construct bioreactor 10 is oriented with cell attachment matrix 20 tilted at an angle that allows gas to exit from the underside of cell attachment matrix 20. Tissue construct bioreactor 10 could remain in this position throughout the culture, provided cells have attached to cell attachment matrix 20.

Figure 9:
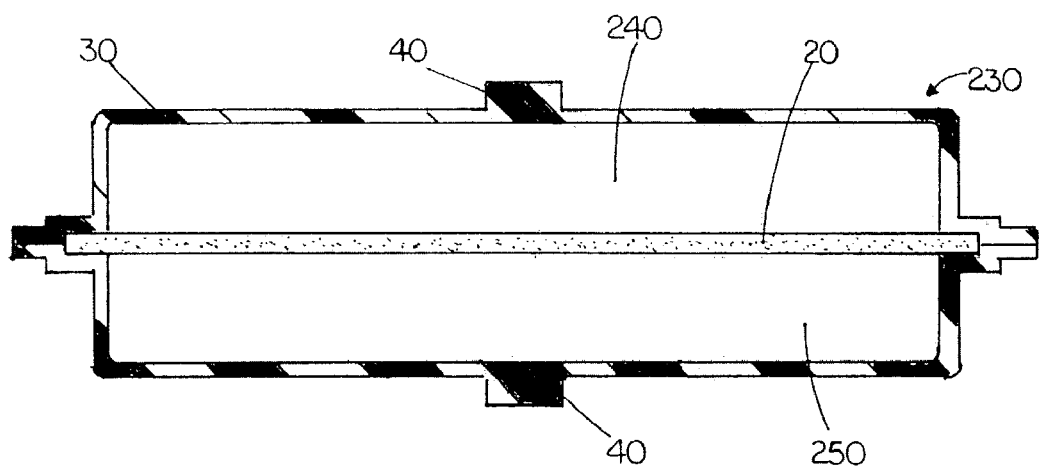
FIG. 9 shows an embodiment of a compartmentalized tissue construct bioreactor configured to allow independent access to each compartment.

FIG. 9 shows an embodiment of a compartmentalized tissue construct bioreactor configured to allow independent access to each compartment. Compartmentalized tissue construct bioreactor 230 houses cell attachment matrix 20 in a predetermined position and in a manner that creates first compartment 240 and second compartment 250. As previously described, if the tissue construct bioreactor walls are flexible, one access port can be used to access each compartment with a needle or a syringe without exposure to airborne contaminants. More ports may be desirable depending the objectives of medium delivery, which include rates of fluid delivery and removal, distribution of metabolites, distribution of cells in inoculum, and removal of undesired gas. In this embodiment, tissue construct bioreactor walls 30 are flexible, and access ports 40 are configured to form a seal with liquid handling equipment.

Each side of cell attachment matrix 20 can contain the same type of cell, or different types of cells, or one side may have no cells. Each compartment can house a different type of medium, or the same type of medium. Medium can comprise a liquid containing soluble nutrient substrates, or compounds used to elicit a response in the construct, such as when challenging a skin construct with an allergen, or fluid such as gas.

Figure 10:
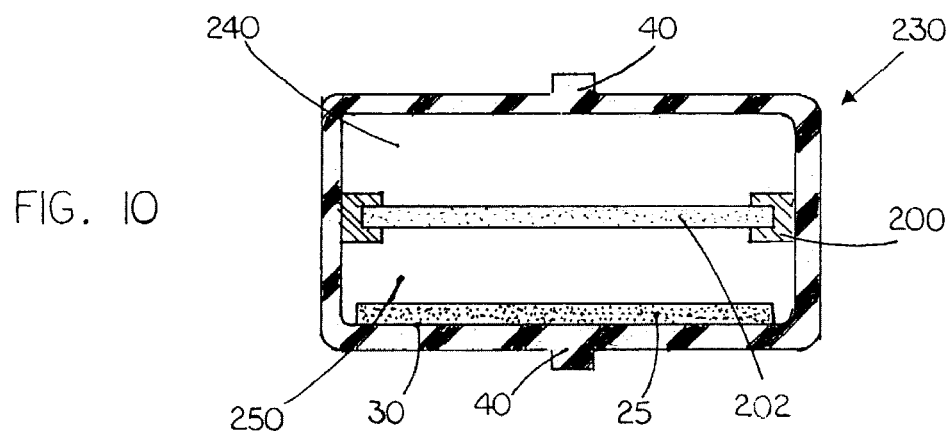
FIG. 10 shows an embodiment in which a tissue construct bioreactor is compartmentalized by a membrane.

FIG. 10 shows an embodiment in which compartmentalized tissue construct bioreactor 230 is compartmentalized by membrane 202. It is advantageous relative to the embodiment described in FIG. 7 when it is desirable to orient the bioreactor in non-horizontal position or when complete isolation of the compartments by membrane 202 is desired. Membrane 202 can function as the cell attachment matrix. Use of membrane 202, as described previously, allows specific environmental conditions to be established for cells that grow in suspension those that are adherent. For example, when a particular cell type is secreting a cytokine that conditions the cell culture medium favorably, the use of a membrane that retains the cytokine in proximity of the cell could be beneficial. As another example, if TGF beta is introduced into one compartment, a semi-permeable membrane with a molecular weight cutoff less than that of the TGF beta can be used to retain the TGF beta in that compartment. In other cases, the transfer characteristics of a membrane are based on the desire to allow transfer from one compartment to another, such as when TGF beta is produced by cells in one compartment and used to stimulate activity of cells in the other compartment. In this case, the membranes molecular weight cutoff would need to exceed the size of TGF beta. For example, if TGF beta were about 25,000 MW, a membrane of 30,000 MWCO would allow TGF beta to cross the membrane. The use of microporous membranes may also be desired when evaluating the absorption of a drug introduced into the compartment in which cells reside confluently upon the membrane. Monitoring the other compartment for presence of the drug can indicate the capacity of the drug to diffuse through the cell mass. Another application could be the culture of skin on one side of the membrane and exposure of the skin to selective compounds to monitor skin reaction as an alternative to animal testing. The use of semi-permeable or microporous membranes can also be useful for co-culture of cells as previously described. In these applications, the membrane can function as both the cell attachment matrix and a barrier to cells, molecules and compounds of a predetermined size. Optional lower cell attachment matrix 25, which in its most simple form may be a portion of lower tissue construct bioreactor wall 30, allows cells to reside in second compartment 250.

Cutting a tissue construct to a specific shape after culture can be desirable when the cell attachment matrix is prone to geometry changes during processing. For example, collagen has a tendency to contract as cells proliferate upon it. When unconstrained throughout the culture period, this results in a change in shape after the onset of culture. Post processing is then needed if a predetermined shape is desired. For example, in the culture of living skin, it can be desirable to create tissue with relatively straight edges so that the skin can be laid side by side on a target sight without the presence of untreated gaps. If the skin construct acquires an edge that is not straight due to a shape change in the cell attachment matrix during culture, post processing to create a straight edge can be achieved by cutting the construct. Cutting a tissue construct to a specific shape after culture can also be desirable when there are regions of the cell attachment matrix that are unwanted in the final construct. For example, constraining the cell attachment matrix during culture, to retain its shape, maintain it in a fixed location for inoculation or optimal feeding, or for any other reason will lead to sections of the cell attachment matrix that are in contact with the constraining member. Post culture, the sections of the cell attachment matrix that are not in contact with the constraining member can differ from the sections of the cell attachment matrix that are in contact with the constraining member. Thus, it may be desirable to remove that section prior to further use of the construct.

Figure 11:
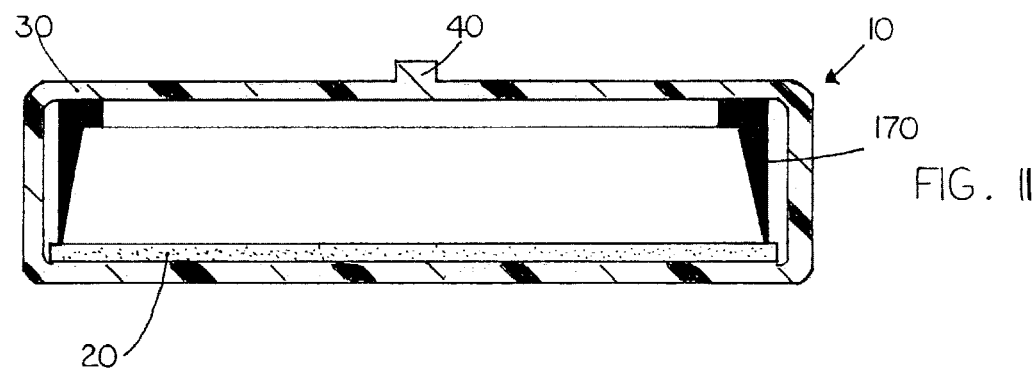
FIG. 11 shows an embodiment of a tissue construct bioreactor configured to cut a cell attachment matrix to a desired shape without any need to first remove the tissue construct from the tissue construct bioreactor.

Advantages of these inventions include the ability to perform processing operations in a closed container, thereby minimizing the risk of contamination and damage that may occur from additional handling of the construct. FIG. 11 shows an embodiment of a tissue construct bioreactor configured to cut a cell attachment matrix to a desired shape without any need to first remove the tissue construct from the tissue construct bioreactor. Cutting die 170 resides within tissue construct bioreactor 10. Post tissue construct processing, cutting die 170 can be driven into cell attachment matrix 20 in order to cut the tissue construct to a desired shape. A design objective is to perform the cutting process without need to open tissue construct bioreactor 10, thereby minimizing contamination risk. A force can be applied to the upper tissue construct bioreactor wall 30 to drive cutting die 170 through cell attachment matrix 20. If tissue construct bioreactor wall 30 is comprised of a flexible material, care should be taken to ensure that the material is not damaged during the cutting process. If tissue construct bioreactor wall 30 is comprised of a rigid material, the upper tissue construct bioreactor wall can move relative to the lower tissue construct bioreactor wall in order to drive cutting die 170 through tissue construct matrix 20. Motion between the upper and lower sections of tissue construct bioreactor 10 should occur without a breach of sterility. Those skilled in the art will recognize that there are many methods of driving cutting die 170 in a manner that maintains sterility. Mechanical design solutions that can be employed to create the appropriate motion include piston type movement and die set mechanisms. For example, the techniques used to obtain motion in a die set can by used when tissue construct bioreactor 10 is not structured to allow any motion between upper and lower tissue construct bioreactor walls 30. In this approach, posts attached to the cutting die would project through one tissue construct bioreactor wall 30 in a sealed manner. Each post would be capable of moving perpendicular to the plane of the bioreactor wall and be sealed at the point where it projects through the bioreactor wall to maintain bioreactor sterility. Applying a force to the posts would in turn drive the cutting die through the cell attachment matrix.

Cutting die 170 can reside either constrained or unconstrained within tissue construct bioreactor 10. If unconstrained, care should be taken to ensure that cutting die 170 does not damage cell attachment matrix 20 at any time prior to cutting. Also, care should be taken during the cutting process to ensure that cutting die 170 does not make a partial cut of the tissue construct, as would occur if cutting die 170 perimeter did not reside entirely upon cell culture matrix 20 at the onset of cutting. If constrained, cutting die 170 should be free to move in the direction normal to the plane in which cell attachment matrix 20 resides. Side to side movement once cutting die 170 makes contact with cell attachment matrix 20 may be needed to cut cell attachment matrix 20 depending on factors such as the strength of cell attachment matrix 20 and the sharpness of cutting die 170.

Figure 12:
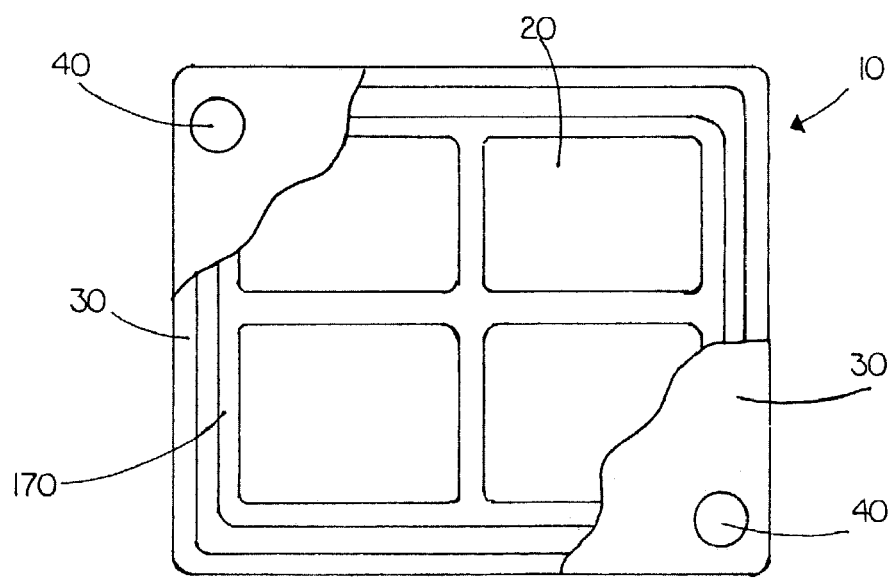
FIG. 12 shows a cutaway view of an embodiment in which a cutting die is configured to cut a cell attachment matrix into multiple sections.

FIG. 12 shows a cutaway through the top view of an embodiment in which cutting die 170 is configured to cut cell attachment matrix 20 into multiple sections. Care should be taken to ensure that cell seeding and cell proliferation are not hindered by cutting die 170.

FIG. 13A and FIG. 13B show one example of an embodiment of a tissue construct bioreactor comprising two compartments and a cutting die useful for separating the desired portion of the cell attachment matrix from the undesired portion. In this embodiment, cell attachment matrix 20 is constrained by frame 200, creating a portion that is undesirable for use in the intended application. The desired portion of the cell attachment matrix is separated from the undesired portion while the tissue construct bioreactor remains a closed system. Cutting die 170 resides in first compartment 240, positioned such that is does not interfere with cell seeding or cell proliferation. At a predetermined stage of tissue construct processing, such as post culture, post cyropreservation, or post shipping the construct to a point of use, cutting die 170 is driven thru cell attachment matrix 20 thereby cutting cell attachment matrix 20 to a desired shape. In this configuration, as best shown in FIG. 13B, the portion of frame 200 that resides in second compartment 250 is designed to form an interference fit with cutting die 170, thereby creating a die set. The illustration of FIG. 13A and FIG. 13B show a cutting process when tissue construct bioreactor walls 30 are comprised of a rigid material. However, the cutting process can also occur in a closed system when at least one wall of the tissue construct bioreactor is free to move relative to the opposing wall in a manner that does not breach sterility, such as that shown in FIG. 3. In the case where neither wall of the tissue construct bioreactor is free to move, cutting die 170 can be driven by way of posts projecting through the wall. Care should be taken to ensure that contamination is prevented by sealing the posts to the wall, by using O-rings or other seal mechanisms known to those skilled in the art.

FIG. 14A and FIG. 14B show cross-sectional views of an embodiment in which tissue construct bioreactor 10 is configured to allow cell attachment matrix 20 to be removed. In this configuration, bioreactor lid 260 is hinged to lower bioreactor body 270. Moveable latch 290 secures bioreactor lid 260 and bioreactor body 270 together. Lid seal 280 prevents contaminants from entering tissue construct bioreactor 10. When moveable latch 290 is repositioned, as shown in FIG. 14B, bioreactor lid 260 can open to allow cell attachment matrix 20 to be removed. In the case where cell attachment matrix 20 resides in a frame, and has not been die cut, the entire frame can be removed to ease handling.

Cell attachment matrix 20 should be structured for removal according to the needs of a particular application. Thus, cell attachment matrix 20 may be captured entirely about its perimeter, partially captured, or reside in a completely un-captured state. For example, it may be desirable to capture cell attachment matrix 20 in a frame so that it can be handled in a manner that does not require direct physical contact with cell attachment matrix 20. In this manner, physically moving cell attachment matrix 20 can be achieved by making contact with frame 200, and not cell attachment matrix 20. There are also applications in which it is preferred that cell attachment matrix 20 is completely detached, and those in which it should be partially detached. For example, when living skin is to be physically positioned on a patient, any mechanism that had previously held it in position must first be removed. Doing so while it resides within the tissue construct bioreactor, such as by die cutting it, is advantageous in terms of minimizing contamination risk and potential tissue construct damage. If the living skin has a specific side that should face the patient when positioned, a partial cut can be helpful. In this method, the majority of the cell attachment matrix comprised of living skin would be pre-cut while residing in the closed tissue construct bioreactor. For example, three sides of a square or rectangular cell attachment matrix could be pre-cut while residing in the tissue construct bioreactor. Subsequently, the living skin would be removed from the tissue construct bioreactor by handling the frame. The frame would be designed in a non-symmetric manner, with text, color-coding, or some other features that clearly indicates the orientation of the living skin. The frame and living skin would be positioned upon the patient in the correct orientation, and the living skin would be fully removed from the frame by use of an instrument such as a scalpel.

FIG. 15A and FIG. 15B show the inoculation and feeding stages of an embodiment of a tissue construct bioreactor in which cell attachment matrix 20 is held in a desired position by frame 200. Frame 200 has vertical walls 310, which combined with cell attachment matrix 20 act to form a first compartment 240. In this embodiment, frame 200 is configured for gravitational seeding in which all of the inoculum resides directly above cell attachment matrix 20. Vertical side walls 310 of frame 200 are designed to retain inoculum 220 in a manner that minimizes cell seeding onto the walls of frame 200 while positioning inoculum 220 directly above cell attachment matrix 20. This configuration achieves an objective of minimizing cell deposit on surfaces other than cell attachment matrix 20. Vertical walls 310 are of a height such that a predetermined volume of inoculum will be retained in first compartment 240.

As shown in FIG. 15A, inoculum 220 enters first compartment 240 by way of access port 40. Cells settle out of inoculum 220 onto cell attachment matrix 20. Frame 200 should be designed to capture cell attachment matrix 20 in a manner that retards the passage of inoculum 220 through the interface between frame 200 and cell attachment matrix 20 and into second compartment 250. The amount of inoculum 220 that can pass through this interface and still result in an acceptable seeding pattern is dependent upon several factors including cell density, inoculum volume, seeding rate, perimeter length, cell attachment matrix 20 surface area, and cell attachment matrix 20 liquid permeability. If no cell passage through this interface is desired, the cell support matrices should be so structured. For example, a 70 Shore A durometer elastomeric gasket, residing on both the upper and lower halves of frame 200, was able to prevent liquid passage when the cell attachment matrix was 0.020 thick bovine collagen squeezed to 50% of its original thickness.

In FIG. 15B, cell culture medium 70 has been added to second compartment 250. In this case, the volume of culture medium 70 added to second compartment 250 is such that is has risen above vertical walls 310 and overflowed into first compartment 240. Medium can be isolated in first compartment 240 and second compartment 250 by keeping the volume of medium below the top of vertical side walls 310. In this manner, one type of medium could reside in first compartment 240 and another type of medium could reside in second compartment 250.

In some configurations, the distance between the cell attachment matrix and the tissue construct bioreactor wall may not be constant. This may occur for a variety of reasons. An example would be when the distance between the wall and the cell attachment matrix creates a capillary attraction in the presence of liquid that causes either the wall or the matrix, or both, to be drawn towards each other. Other examples include the cell attachment matrix not having the mechanical strength to retain a planar position and therefore sagging in unconstrained areas, or the tissue construct bioreactor wall not having the mechanical strength to retain a planar position and sagging in unconstrained areas. If the non-uniform spacing occurs, inoculation will result in differing seeding densities across the surface of the cell attachment matrix since the volume of inoculum residing above the matrix will vary.

In the case where the tissue construct bioreactor wall is flexible and can be driven towards the cell attachment matrix, such as when external pressure exceeds internal pressure or when capillary action draws it towards the cell attachment matrix, it can be constrained such that it resides substantially within a given plane by connecting it to a rigid outer shell. When the tissue construct bioreactor wall is gas permeable, the rigid outer shell should be configured such that the minimal contact with the gas permeable portion of the tissue construct bioreactor wall needed to retain the desired degree of planar position is attained. In this manner, the maximum gas contact with the gas permeable wall is allowed. In FIG. 16, non-flexible outer housing 330 mates with flexible tissue construct bioreactor wall 30 at predetermined points. Boss 340 of flexible tissue construct bioreactor wall 30 is secured to pocket 350 of outer housing 330. Care should be taken to ensure that gas compartment 140 has an appropriate cross sectional area for the desired application, and that the distance between the tissue construct bioreactor gas permeable wall 30 and outer housing 330 allows adequate gas exchange. Prototypes using a 100 sq. cm., 0.004 inch thick dimethyl silicone bioreactor wall, provided adequate gas exchange to support 600 billion murine hybridoma cells when the cross-section was comprised of numerous 0.046 inch projections from outer housing 330 that supported a diamond weave mesh comprised of 0.020 inch strands at 16 strands per inch. The ratio of the upper surface of the projections to the surface they projected from was about 1:5. Four symmetrically located circular gas access openings, 0.32 inches in diameter through the surface of outer housing 330, covered with 0.2 micron sterile filters, allowed adequate passive gas exchange for cell culture when the bioreactor resided in a 5% CO2 incubator at 37° C. For design estimates, an initial estimate of the appropriate cross-sectional area and distance can be made by referencing a particular cells metabolic activity against the metabolic activity of murine hybridoma cells, and normalizing for the target quantity of viable cells using the described dimensional information.

Figure 17:
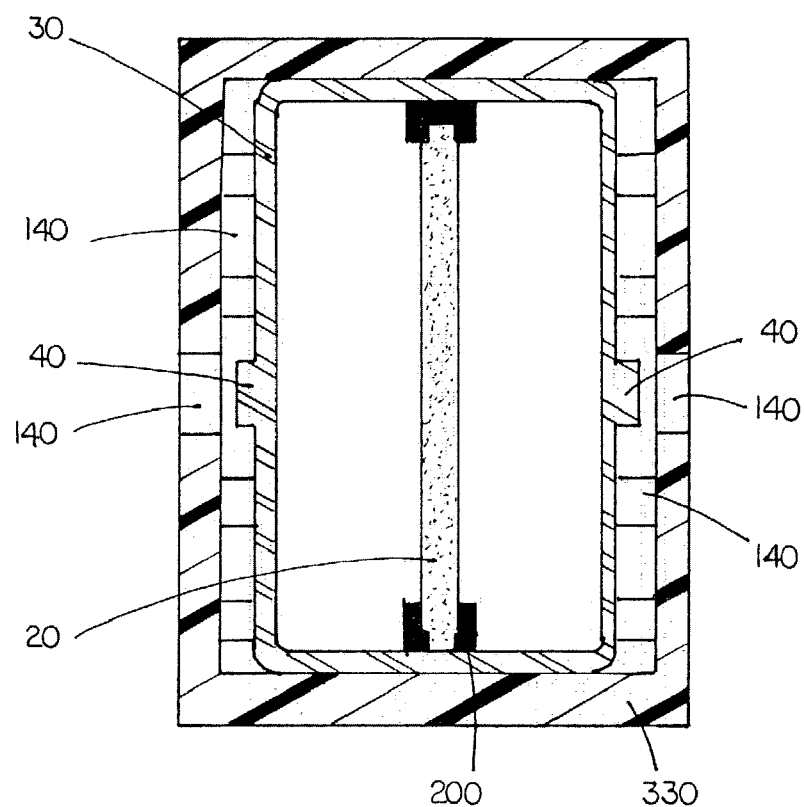
FIG. 17 shows a tissue construct bioreactor with walls constrained in a planar state by an outer housing.

When it is desirable to constrain the flexible gas permeable tissue construct bioreactor walls in a substantially planar state, such as when oriented in the horizontal position while containing liquid or when internal pressure exceeds external pressure, boss 340 and pocket 350 can be eliminated from outer housing 330, as best shown in FIG. 17.

Figure 18:
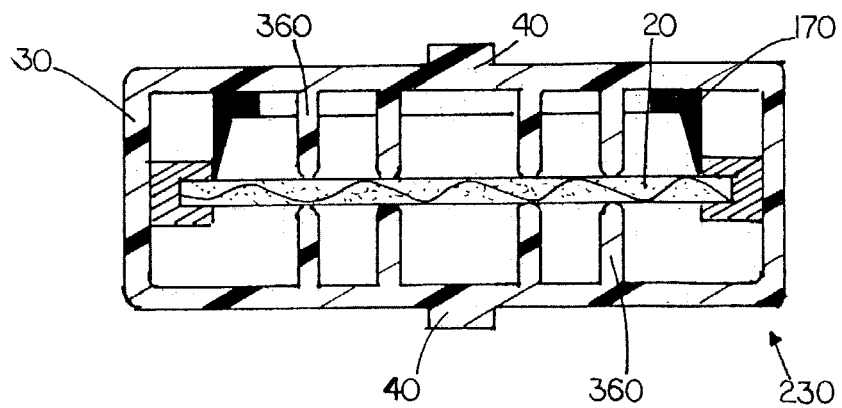
FIG. 18 shows another configuration for maintaining a relatively parallel geometric relationship and fixed minimum distance between a cell attachment matrix and the walls of a flexible tissue construct bioreactor.

FIG. 18 shows another configuration for maintaining a relatively parallel geometric relationship and fixed minimum distance between cell attachment matrix 20 and flexible tissue construct bioreactor wall 30. Spacer projections 360 extend from flexible tissue construct bioreactor wall 30 a predetermined distance. Spacer projections 360 act to maintain a fixed minimum distance between flexible tissue construct bioreactor wall 30 and cell attachment matrix 20. To avoid the inhibition of cell deposit and growth, the geometry of spacer projection 360 should be such that minimal contact with cell attachment matrix 20 is achieved while maintaining the desired degree of parallelism. In this configuration, cutting die 170 is unobstructed by spacer projections 360.

Figure 19:
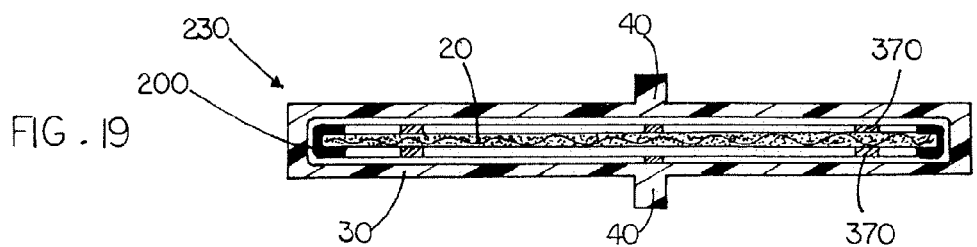
FIG. 19 shows a configuration in which a grid is used to maintain a relatively parallel relationship and fixed minimum distance between a cell attachment matrix and a flexible tissue construct bioreactor wall.

FIG. 19 shows a configuration in which grid 370 is used to maintain a relatively parallel relationship and fixed minimum distance between cell attachment matrix 20 and flexible tissue construct bioreactor wall 30. The geometry of grid 370 should be such that it makes minimal contact with cell attachment matrix 20 while maintaining the desired degree of parallelism. Grid 370 can be any type of biocompatible material, and may be a separate component or part of another component, such as frame 200. Grid 370 should be configured so that exposed sections of cell attachment matrix 20 can be removed when the tissue construct is ready for further processing or use in an application. Because contact with grid 370 could affect cell seeding and proliferation, those sections of cell attachment matrix 20 immediately adjacent to grid 370 should only be used after demonstrating that those specific sections are suitable for use in the intended application.

Figure 20:
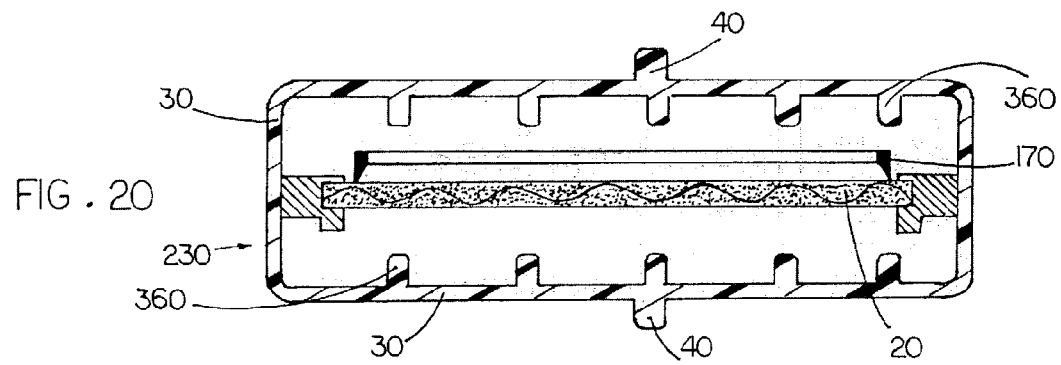
FIG. 20 shows a tissue construct bioreactor configured to maintain a cell attachment matrix from contacting the walls of a tissue construct bioreactor and to allow the cell attachment matrix to be cut to a desired shape.

While the configurations described in FIG. 18 and FIG. 19 allow a minimum distance to be maintained between cell attachment matrix 20 and flexible tissue construct bioreactor wall 30, these configurations may be operated in excess of the minimum distance by adding fluid volume to the tissue construct bioreactor, thereby driving flexible tissue construct bioreactor wall 30 away from cell attachment matrix 20. FIG. 20 shows tissue construct bioreactor 10 in this condition. Note that the spacer projections 360 do not make contact with cell attachment matrix 20.

Figure 21A:
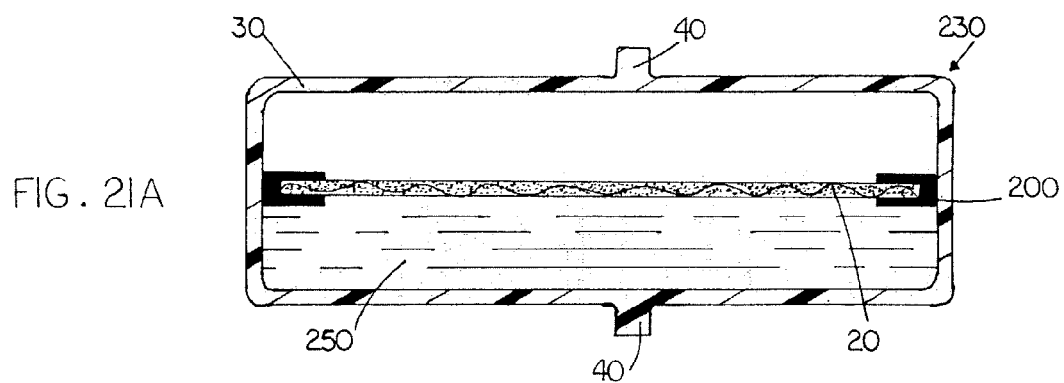
FIG. 21A and FIG. 21B show a method of inoculating one side of a cell attachment matrix residing within a compartmentalized tissue construct bioreactor.
Figure 21B:
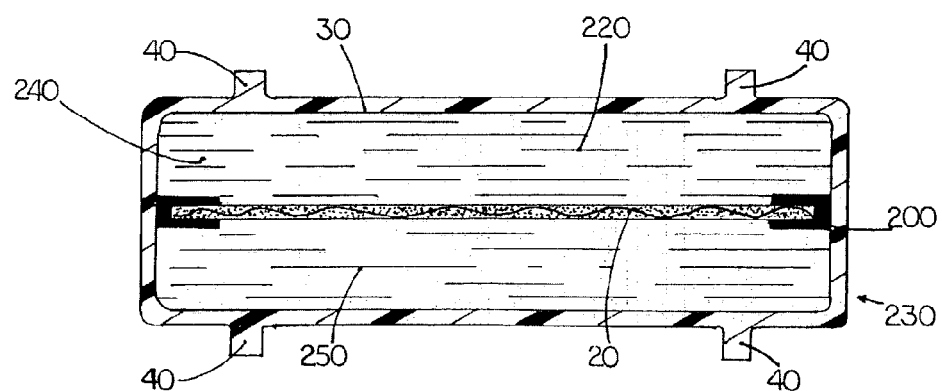

FIG. 21A and FIG. 21B show a method of inoculating one side of a cell attachment matrix residing within a compartmentalized tissue construct bioreactor. In FIG. 21A, second compartment 250 of compartmentalized tissue construct bioreactor 230 is filled with a predetermined volume of liquid, such that cell attachment matrix 20 resides in a generally planar state when compartmentalized tissue construct bioreactor 230 is oriented in a horizontal position. In FIG. 21B, first compartment 240 is then filled with inoculum 220. Inoculum 220 can seed onto cell attachment matrix 20 by gravity, while compartmentalized tissue construct bioreactor 230 is oriented in a horizontal position, or by centrifugation as previously described.

Figure 22A:
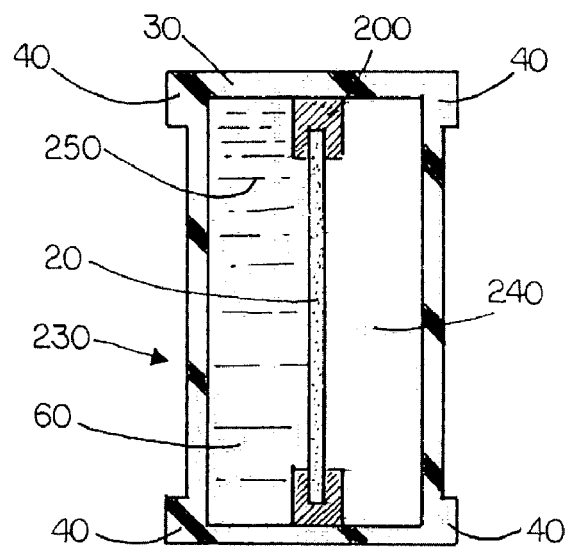
FIG. 22A and FIG. 22B show a method of inoculating two sides of a cell attachment matrix residing within a compartmentalized tissue construct bioreactor.
Figure 22B:
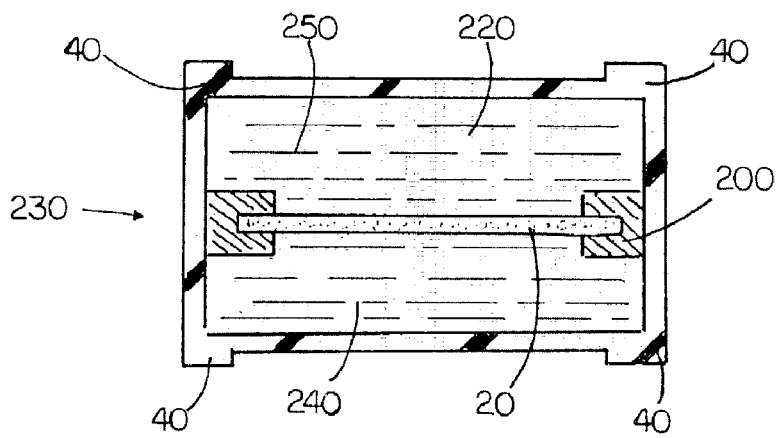

FIG. 21A and FIG. 21B, combined with FIG. 22A and FIG. 22B, show a method of inoculating two sides of a cell attachment matrix residing within a compartmentalized tissue construct bioreactor. As shown in FIG. 21A, second compartment 250 of compartmentalized tissue construct bioreactor 230 is filled with a predetermined volume of liquid, such that cell attachment matrix 20 resides in a generally planar state when compartmentalized tissue construct bioreactor 230 is oriented in a horizontal position. As shown in FIG. 21B, first compartment 240 is then filled with inoculum 220. Cells from inoculum 220 can seed onto cell attachment matrix 20 by gravity, while compartmentalized tissue construct bioreactor 230 is oriented in a horizontal position, or by centrifugation as previously described. As best shown in FIG. 22A, compartmentalized tissue construct bioreactor 230 is oriented in a position that allows second compartment 250 to be filled with gas 60 in a manner that displaces the liquid that was present during the initial seeding of cell attachment matrix 20. Subsequently, compartmentalized tissue construct bioreactor 230 is oriented in a horizontal position and the liquid of first compartment 240 acts to retain cell attachment matrix 20 in a generally planar state. Second compartment 250 is then filled with inoculum 220 as shown in FIG. 22B. Inoculum residing in second compartment 250 can seed onto cell attachment matrix 20 by gravity, while compartmentalized tissue construct bioreactor 230 is oriented in a horizontal position, or by centrifugation as previously described.

Seeding a cell attachment matrix within a non-compartmentalized tissue construct bioreactor, when the density of the cell attachment matrix exceeds that of the cell culture medium, can be achieved by the use of gravity. As shown in FIG. 23, inoculum 220 is placed in tissue construct bioreactor 10. Cell attachment matrix 20 settles by gravity to the interior surface of lower tissue construct bioreactor wall 30. Cells settle out of inoculation by gravity onto the exposed face of cell attachment matrix 20 as shown in FIG. 23A. In the case where it is desirable to seed two sides of cell attachment matrix 20, inoculum is removed post seeding of the first side of cell attachment matrix 20 by any of the methods described previously. Thus, tissue construct bioreactor 10 is temporarily in the compressed position of FIG. 23B. Subsequently, tissue construct bioreactor 10 is turned upside down post cell attachment, and a new inoculum 220 is placed into tissue construct bioreactor 10 such that is it exposed to the second face of cell attachment matrix 20 as shown in FIG. 23C. To prevent cell attachment matrix 20 from getting out of plane, tissue construct bioreactor walls 30 can be flexible, and tissue construct bioreactor 10 can be squeezed such that tissue construct bioreactor walls 30 constrain cell attachment matrix 20 in a planar state while tissue construct bioreactor 10 is turned over. Subsequently, cell attachment matrix 20 is retained by gravity in proximity to the interior surface of lower tissue construct bioreactor wall 30. Cells settle out of inoculation by gravity onto the exposed face of cell attachment matrix 20.

FIG. 24 shows and embodiment for seeding two sides of a cell attachment matrix when it is desirable to minimize cell attachment to surfaces other than that of the cell attachment matrix. As shown in FIG. 24A, frame 200 is configured with vertical walls 310 that retain inoculum 220 directly above cell attachment matrix 20 in first compartment 240. The outlet of access port 40 is configured such that it resides above a portion of cell attachment matrix 20 allowing inoculum 220 to be dispensed to the interior of the perimeter of frame 200, and thus above cell attachment matrix 20. If a needle is used to dispense inoculum, access port 40 may reside in a position other that directly over a portion of cell attachment matrix 20 so long as the tip of the needle resides over a portion of cell attachment matrix 20 during inoculum 220 delivery. Post seeding, tissue construct bioreactor 10 is turned upside down and new inoculum 220 is placed into tissue second compartment 250 through a second access port 40, configured as previously described, such that when inoculum 220 is delivered it resides over the exposed surface of cell attachment matrix 20. As shown in FIG. 24B, cell culture medium 70 is delivered by way of a first access port 40 such that it resides at a level that covers the lower face of cell attachment matrix 20, but does not commingle with inoculum 220. If gas becomes trapped at the lower surface of cell attachment matrix 20, it can be removed by penetrating septum 80 of the lower access port 40 with a needle, slightly tilting tissue construct bioreactor 10 such that gas is moved to a the wall of frame 200, placing the tip of the needle into the gas, and withdrawing it. Legs 190 elevate frame 200 such that cell culture medium 70 can displace gas from the underside of cell attachment matrix 20.

Fluid can be delivered into the tissue construct bioreactors described herein in a batch or continuous manner, and in an automated or manual manner. In the case of a compartmentalized tissue construct bioreactor, continuous or batch feeding can occur on one side only, on both sides, or across the tissue construct. In the configuration shown in FIG. 25, access needles 380 enter compartmentalized tissue construct bioreactor 230 by penetrating septum 80 of access ports 40. Compartmentalized tissue construct bioreactor 230 is oriented in a vertical position to allow gas to exit. Fluid can be delivered to each compartment from an independent source, or multiple tissue construct bioreactors can receive fluid from a common source depending on the objectives of a given application.

Figure 25:
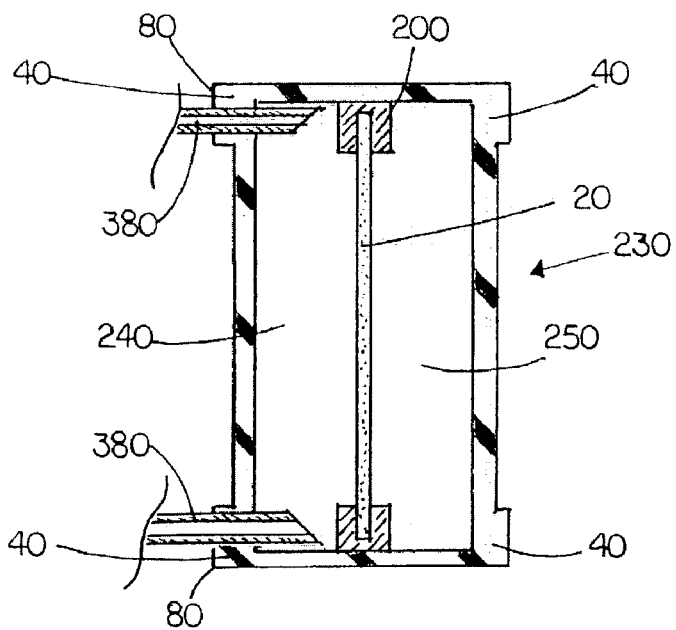
FIG. 25 shows an embodiment of a compartmentalized tissue construct bioreactor configured for needle access.
Figure 26A:
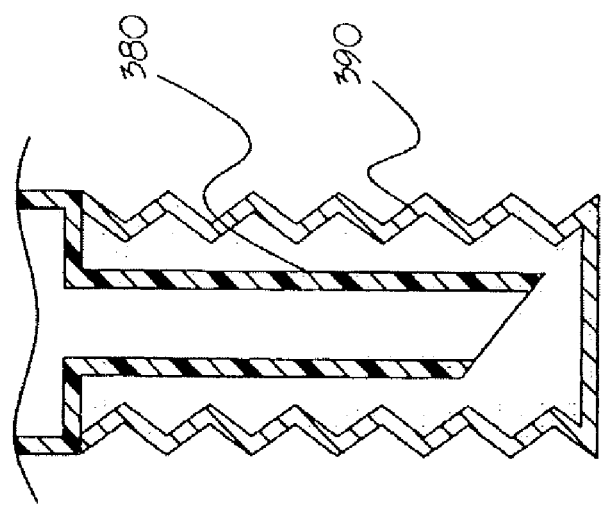
FIG. 26A, FIG. 26B, and FIG. 26C show an embodiment for needle access that minimizes exposure to contamination.
Figure 26B:
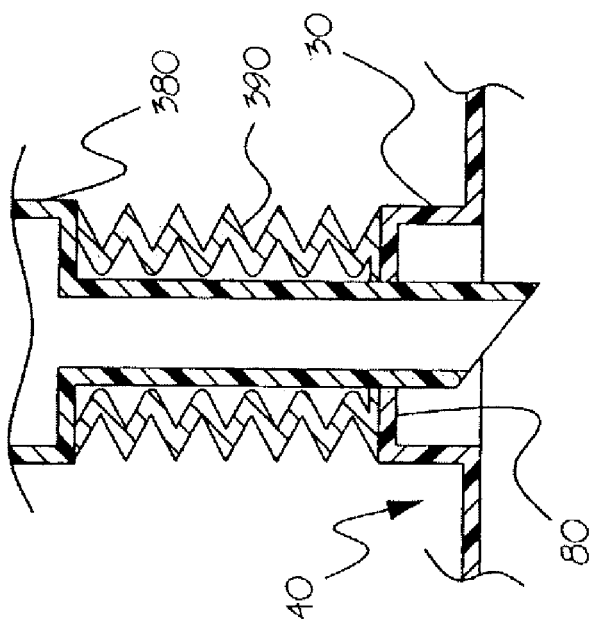
Figure 26C:
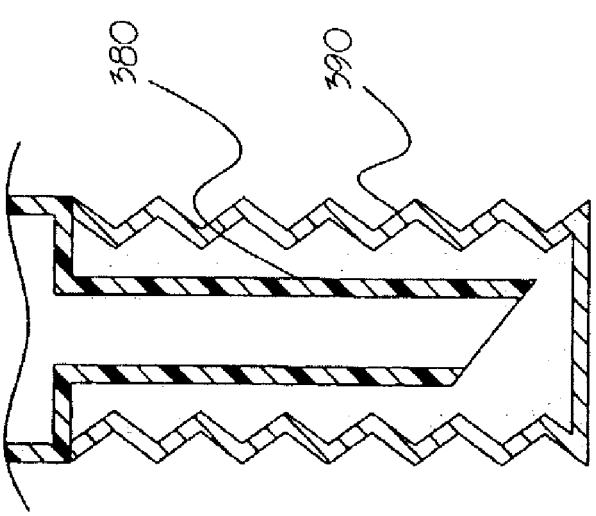

FIG. 26 shows an embodiment of an invention for minimizing contamination in applications in which a needle penetrates a septum to access the tissue construct bioreactor. FIG. 25 shows access needles 380 engaged in tissue construct bioreactor 230. FIG. 26A shows an enlarged view of one access needle 380 prior to penetration of tissue construct bioreactor 230. Access needle protection septum 390 protects access needle 380 from contamination. FIG. 26B shows access needle 380 fully engaged in the septum 80 of access port 40. Access needle protection septum 390 has recoiled as a result of contact with the face of septum 80 and has altered its position relative to the tip of needle 380. FIG. 26C shows access needle 380 after removal from access port 40. Access needle protection septum 390 has returned to its original position thus protecting access needle 380 from contamination. Access needle protection septum 390 can be bellows shaped, spring loaded, or adapted by any other method that provides a force that drives access needle protection septum 390 into a position such that its face extends beyond the tip of needle 380 when needle 380 is not engaged in access port 40. Importantly, the force driving access needle protection septum 390 is such that the face of access needle protection septum 390 makes contact with the face of septum 80 during penetration, fluid access, and withdrawal.

Minimizing the risk of contamination is a very important factor in cell culture as well as in the tissue construct bioreactor designs. More than one access port can be used to gain access to fluid residing in the tissue construct bioreactors disclosed herein. However, configuring the access ports of the tissue construct bioreactor so that airborne contaminants do not enter the tissue construct bioreactor when adding or removing fluid can reduce contamination risk. If only one access port is needed for fluid access, contamination risk can be further reduced. The access port(s) can be configured to seal the tissue construct bioreactor from airborne contaminants during fluid handling by designing it to create a seal with fluid handing equipment. If at least one of the tissue construct bioreactor walls is comprised of a flexible material, the volume of the tissue construct bioreactor will self adjust as fluid is added and removed. If the tissue construct bioreactor is comprised of non-flexible material, fluid can still be added or removed using one port that is sealed to liquid handling equipment by configuring the tissue construct bioreactor such that its volume can be altered as best shown in FIG. 3. In this manner, fluids can be added and removed through one port without changing the pressure within the tissue construct bioreactor.

In the tissue construct bioreactor configurations of this invention, each access port is preferably configured to provide a sealed interface with typical fluid handling equipment, such as a pipette, syringe, syringe needle, perfusion circuit tubing, or perfusion circuit manifolds. For example, a luer lock or penetrable septum would achieve that purpose. When interfacing with a pipette, the access port should be configured to allow the pipette to remain attached to the vacuum pipettor when withdrawn. Also, in order to reduce contamination risk, non-sterile surfaces such as the vacuum pipettor or the technician's hand should not reside directly over the access port when the pipette interfaces with the access port.

Figure 27B:
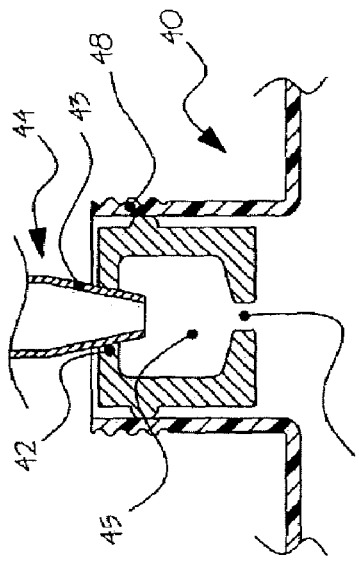
FIG. 27A, FIG. 27B, FIG. 27C, and FIG. 27D disclose configurations of an embodiment for pipette access in a liquid tight manner that allows non-sterile surfaces to reside in areas other than directly above access ports.
Figure 27D:
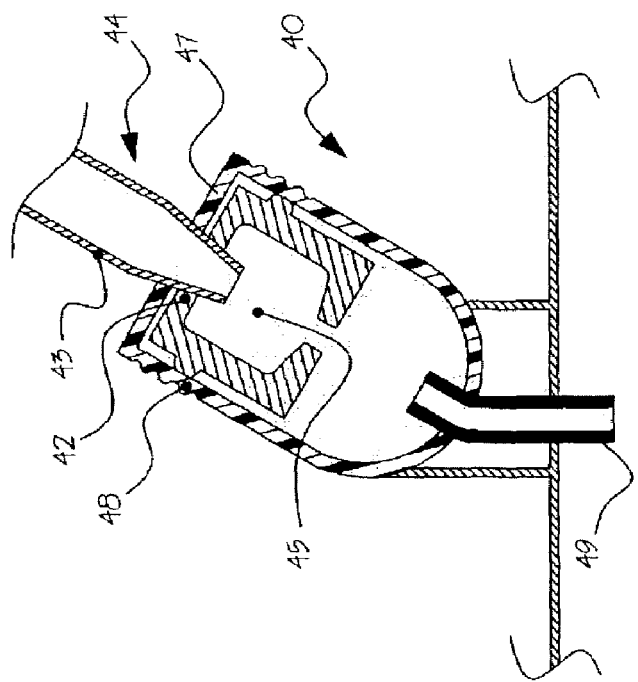
Figure 27A:
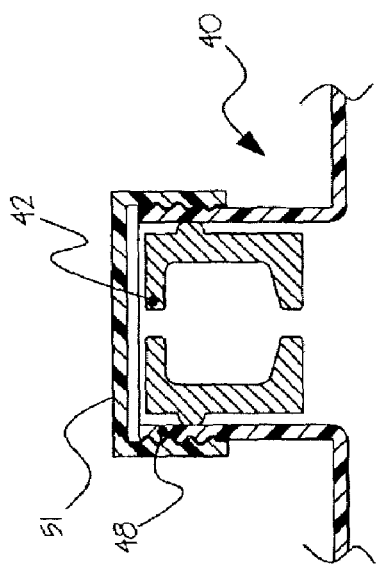

FIG. 27A, FIG. 27B, FIG. 27C, and FIG. 27D disclose configurations of an embodiment for pipette access in a liquid tight manner that allows non-sterile surfaces to reside in areas other than directly above the access port. This invention is not limited to tissue construct bioreactors, but has use in all applications in which a pipette is used to add or remove fluid from a container comprised of flexible material, or a non-flexible vented container, or a container capable of adjusting in internal volume. FIG. 27A shows a cross-sectional view of access port 40. Access port 40 is designed with an elastomeric thin walled access opening 42 capable of expanding in cross-section to create a seal with the tip of a pipette. Threads 48 mate with cap 51 that covers access port 40 when access port 40 is not in use, thereby preventing airborne contaminants from entering access port 40.

FIG. 27B shows pipette tip 43 inserted into thin walled access opening 42 of access port 40. The cross-section of thin walled access opening 42 has increased relative to that of FIG. 27A in order to accommodate pipette tip 43. The seal at the interface of thin walled access opening 42 and pipette tip 43 prevents airborne contaminants from entering the tissue construct bioreactor and allows the volume of the tissue construct bioreactor to be increased and decreased as fluid is added and removed. Thin walled access opening 42 applies a seal force to pipette tip 43. The thin-walled nature of the opening is a design characteristic intended to achieve a seal with less force exerted upon pipette tip 43 than the force exerted to retain pipette 44 in a vacuum pipettor. When the force required to break the seal between pipette 44 and access port 40 does not exceed the force retaining pipette 44 in a vacuum pipettor, pipette 44 will be retained in the vacuum pipettor when it is withdrawn from access port 40.

The force needed to dislodge the pipette from the pipettor can vary depending on the pipette, the pipettor, the amount of wear on the rubber piece in the pipettor that the pipette fits into, and how far the operator inserts the pipette into the pipettor. To assess the variance in force, a pipette was inserted into a pipettor with as little penetration into the pipettor as needed to attain a seal, and as far into the pipettor as it could go. Then the amount of force needed to dislodge the pipette from the pipettor was measured. When the pipette had minimal penetration into the pipettor, the force required to dislodge a 10 ml pipette (Fisherbrand® 13-678-11E) from a pipettor (Integra Biosciences Pipetteboy acu model) was measured at 0.2 lb. When the same pipette had maximum penetration, the force required to dislodge it from the pipettor was measured at 4.2 lb. The thickness and material characteristics of the thin walled access opening 42 will affect the force it applies to pipette 44. For example, tests have demonstrated that when the material thickness of the thin walled access opening is 0.02 inches, and the cross-section is circular with an opening diameter of 0.085 inches, and the material has a durometer of 60 Shore A, a maximally inserted pipette will remain in a vacuum pipettor (Integra Biosciences Pipetteboy acu model) when the tip is removed from thin-wall access opening 42 when the pipette has maximal insertion into the pipettor. When the thin walled access opening 42 became wet, approximately 20% less resistance to pipette removal was encountered indicating that the ratio of material thickness to the diameter of thin walled access opening could be about 30% (i.e. 0.02 inches divided by 0.085 inches times 120%). Void volume 45 is designed such that it makes minimal contact with pipette tip 43 and allows pipette 44 to be inserted at, or rotated to, various angles. Preferably, the majority of gripping force applied to pipette tip 43 should occur from thin walled access opening 42 and not from contact with the walls enclosing void volume 45. Fluid access channel 46 allows unencumbered movement of fluid between the tissue construct bioreactor and pipette 44. In applications with cell suspensions, the volume of fluid access channel 46 can be reduced to minimize the number of cells that reside within it. For example, a 0.031 inch diameter, 0.5 inches long, will allow adequate flow while reducing the void volume. If void volume is not a concern, the cross-sectional area of access channel 46 can exceed that of thin walled access opening 42. If pipette tip 43 does enter fluid access channel 46, less gripping force will be exerted if fluid access channel 46 is a rigid material with a non-circular cross-sectional area, as contact area will be reduced.

Figure 27C:
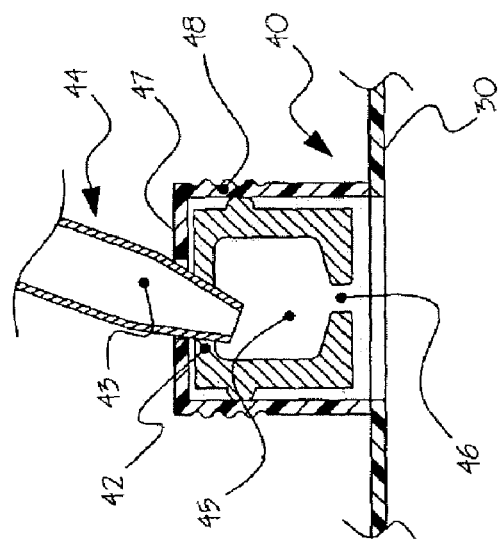

FIG. 27C shows pipette 44 positioned at an angle such that non-sterile surfaces do not reside directly above access port 40. Pipette stop 47 limits the amount of penetration that pipette 44 can make into access port 40. Threads 48 mate with cap 51 that covers pipette stop 47 when access port 40 is not in use, thereby .preventing airborne contaminants from entering access port 40. The opening of pipette stop 47 should be preferably dimensioned such that when pipette tip 43 resides within void volume 45 during fluid handling, and a seal exists between pipette 44 and thin walled access opening 42, pipette 44 is prevented from moving further into access port 40. When pipette stop 47 is present, and dimensioned in the preferred manner, the cross-section of fluid access channel 46 has no effect on the removal force and thus the cross-sectional geometry can be any shape that allows adequate fluid movement. Pipette stop 47 shrouds access port 40, which is sealed to flexible bioreactor wall 30. As pipette 44 is positioned in order to prevent non-sterile surfaces from residing directly above access port 40, the flexible nature of tissue construct bioreactor wall 30, or any other container comprised with a flexible wall, allows access port 40 to be angled without any breach of seal.

FIG. 27D shows another configuration of an embodiment in which pipette 44 is positioned at an angle such that non-sterile surfaces do not reside directly above access port 40. In this depiction, access port 40 sealed to rigid tissue construct bioreactor wall 30, or any other rigid container wall, by way of flexible tube 49. Those skilled in the art will recognize rotating seals that allow movement of access port 40 without breaching sterility are acceptable. The length of pipette stop 47 is preferably such that a technician's fingers, or an instrument such as tweezers, can grip it and move it to a desired angle. Generally, a length of at least 0.25 inches will achieve this purpose. In the case where simplicity is desired, and access port 40 is part of a rigid housing, the entire tissue construct bioreactor can be angled to ensure that non-sterile surfaces do not reside directly above access port 40.

Another method of preventing non sterile surfaces from residing directly above access port 40 during fluid handling is to configure the opening of pipette stop 47 with a dimension slightly larger than the dimension of thin walled access opening 42 that is required to create the desired seal of pipette 44, while still limiting penetration into void volume 45, thereby minimizing undesired force from being exerted on pipette tip 43 by the walls of void volume 45, as best shown in FIG. 27C. In this manner, pipette 44 can be angled without having to reorient the device that access port 40 is attached to. For example, a dimensional opening of pipette stop 47 that is more than 0.010 inches in diameter larger than that of thin walled access opening 42 can achieve the result when interfacing with a 25 ml VWR pipette (catalogue number 53283-710) that is about 12 inches long.

Further reduction in contamination risk can be attained if the tissue construct bioreactor is capable of functioning as a cryopreservation container. To achieve this purpose in the configurations previously described, the tissue construct bioreactor should be comprised of materials commonly used in cryopreservation bags, such as polyethylene, polypropylene, poly-n-butylene, polyisobutylene, poly-4-methylpentene-1, chlorosulfonated polyethylene, polystyrene, halogenated polyethylene, polymethyl metacrylate, ethylene vinyl acetate, polyvinyl chloride and copolymers thereof. Ideally, the tissue construct bioreactor should be designed such that uniform heat transfer occurs throughout the tissue construct. Thus, the walls of the tissue construct should be uniform in thickness to the maximum extent possible. Internal components, such as dies and mechanisms to hold the cell attachment matrix in a desired position, should be located such that they do not impede heat transfer at the surface of the tissue construct. When possible, access ports that cause non-uniformity in the tissue construct bioreactor wall should be positioned such that they do not reside above or below the surface of the cell attachment matrix.

Figure 28:
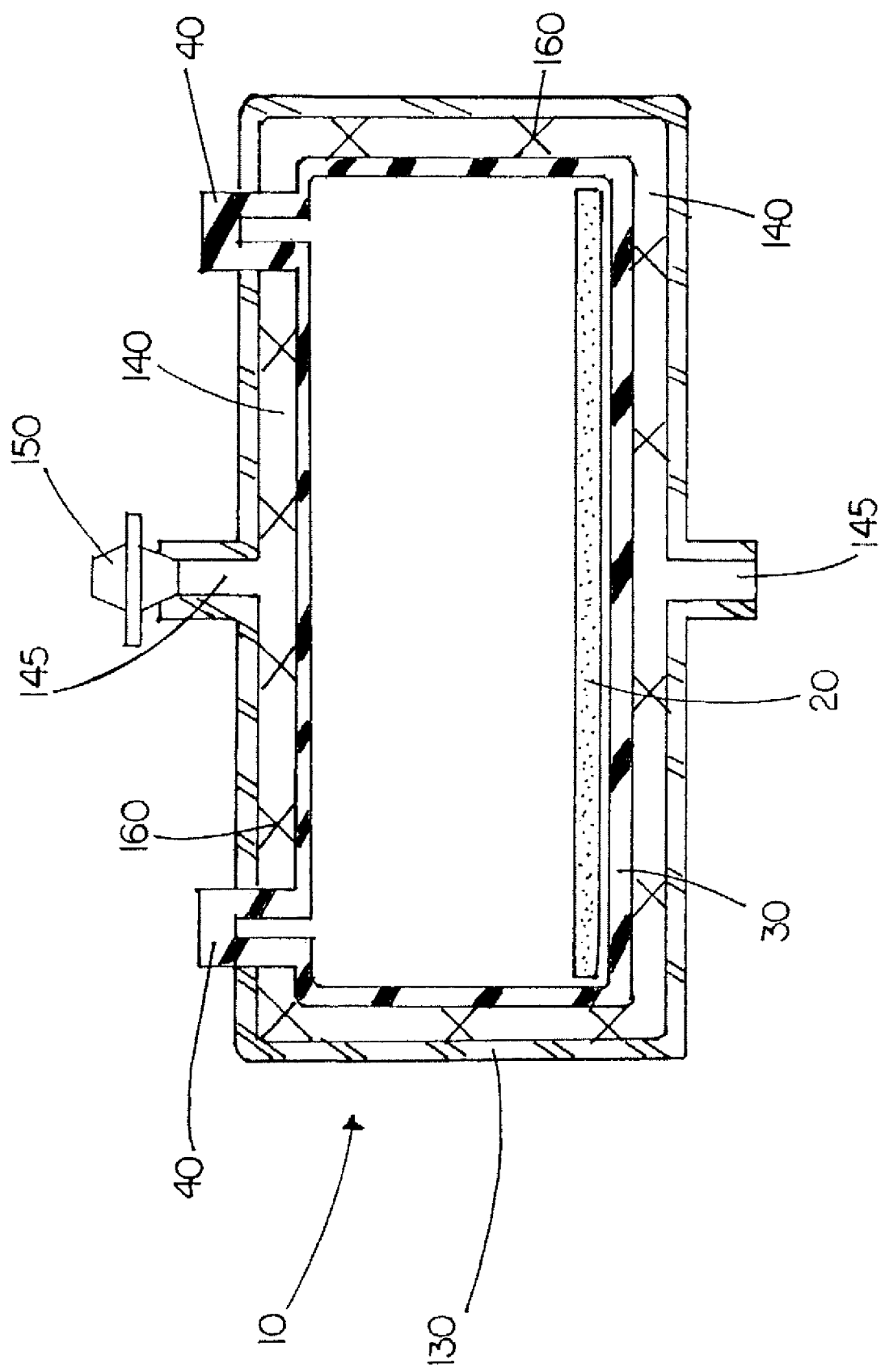
FIG. 28 shows an embodiment of a tissue construct bioreactor adapted for cryopreservation in the case where the material selected for the tissue construct bioreactor walls is not compatible with cryopreservation, or when a redundant seal is desired.

Materials typically used in cryopreservation bags may not be suitable for the tissue construct bioreactor walls in some applications. For example, the gas permeability of those materials is inferior to materials not commonly used for cryopreservation bags, such as silicone. If the tissue construct bioreactor is comprised of material that can be damaged during cryopreservation, the tissue construct bioreactor can still be adapted to allow cryopreservation of the tissue construct without any need to first remove the cell attachment matrix and place it in a cryopreservation bag. FIG. 28 shows an embodiment of a tissue construct bioreactor with additional cryopreservation adaptation in the case where the material selected for tissue construct bioreactor walls 30 is not compatible with cryopreservation, or when a redundant seal is desired. Cryopreservation enclosure 130 incorporates tissue construct bioreactor 10. Cryopreservation enclosure 130 can be any material capable of withstanding the cell culture cryopreservation process. Cryopreservation enclosure 130 should form a sealed enclosure that prevents contaminants from entering, or liquid from leaving, the enclosure. Those skilled in the art will recognize that there are many methods available that are commonly used to form sealed enclosures. Any additional materials selected such as adhesives or o-rings must be compatible with the cryopreservation process and are preferable biocompatible. Preferably, both cryopreservation enclosure 130 and tissue construct bioreactor walls 30 are designed to facilitate uniform heat transfer.

Preferably, the tissue construct bioreactor, cell attachment matrix, and the cryopreservation enclosure are first assembled and then sterilized. In the case where cryopreservation enclosure 130 does not allow adequate gas transfer for a particular tissue construct culture application, gas access to tissue construct bioreactor wall 30 is needed by way of gas compartment 140. Gas compartment 140 should be adapted such that gas can move in and out of it, either by passive diffusion or by forced movement. Preferably, gas exchange takes place without breaching the sterility of gas compartment 140, such as by way of sterile gas filter 150 residing in gas compartment access port 145. In this manner, the tissue construct bioreactor is capable of providing adequate gas exchange by way of gas permeable tissue construct bioreactor wall 30. Gas compartment spacer 160 prevents contact between tissue construct bioreactor wall 30 and cryopreservation enclosure 130 when either tissue construct bioreactor wall 30 or cryopreservation enclosure 130 are comprised of flexible materials. Thus, a space between tissue construct bioreactor wall 30 and cryopreservation enclosure 130 is maintained, forming gas compartment 140.

Preferably, gas compartment spacer 160 is an open structure that retains tissue construct bioreactor wall 30 and cryopreservation enclosure 130 parallel with each other, thereby facilitating a uniform volume of gas residing within gas compartment 40. It allows gas to make contact with tissue construct bioreactor wall 30 to the maximum extent possible. For example, a 0.019 thick diamond weave mesh with 16 strands per inch (Nalle Plastics, Austin Tex.) can be used to allow relatively unrestricted diffusion of gas throughout gas compartment 140.

Prior to cryopreservation, both tissue construct bioreactor 10 by way of access port 40, and gas compartment 140 by way of gas compartment access port 145, can be filled with cryoprotectant in a manner that does not breach sterility. In this manner, if tissue construct bioreactor wall 30 loses the integrity of its liquid tight seal during the cryopreservation process, it is ensured that cryoprotectant, and not gas, makes contact with the tissue construct. If sterile filter 150 is not compatible with cryopreservation, it should be removed and aseptically replaced with a secured plug, such as a luer plug, prior to cryopreservation. If an aseptic technique of removing sterile filter 150 is deemed a contamination risk, sterile filter 150 can be configured with a needle to penetrate a septum. Thus, during removal, the system remains closed.

Care should be taken to assure that all surfaces that reside within cryopreservation enclosure 130 remain sterile. That will ensure that contamination of the tissue construct does not occur if tissue construct bioreactor wall 30 loses the integrity of its liquid tight seal during the cryopreservation process, and cryopreservation material of gas compartment 140 mixes with cryopreservation material of tissue construct bioreactor 10. Preferably, tissue construct bioreactor wall 30 and cryopreservation enclosure 130 parallel with each other leading to a uniform volume of cryoprotectant in contact with the surface of tissue construct bioreactor wall 30 and thereby facilitating uniform heat transfer.

Cryopreservation enclosure 130 is useful for all bioreactors and cell culture devices that are comprised of gas permeable material that will not necessarily maintain integrity during the cryopreservation process. For example, cryopreservation enclosure 130 can integrate a cell culture bag of the types described in U.S. Pat. No. 5,686,304 or the VectraCell™ marketed by Bio Vectra (Canada). The need maintain sterility is best achieved by integrating the cell culture bag into cryopreservation enclosure 130 prior to sterilization. Thus, those skilled in the art will recognize that the previously described attributes and features needed to allow gas access to the cell culture bag, such as those of gas compartment 140, and maintain sterility of the contents of the bag and cryopreservation enclosure 130 including gas compartment 140 when filled with cryoprotectant should be present.

Those skilled in the art will appreciate that numerous modifications can be made thereof without departing from the spirit. Therefore, it is not intended to limit the breadth of the invention to the embodiments illustrated and described. Rather, the scope of the invention is to be determined by the appended claims and their equivalents.

I claim:

1. A tissue construct bioreactor comprising:
   a) a flexible housing having an internal volume, said flexible housing including a liquid impermeable material, an upper wall and a lower wall;
   b) a cell attachment matrix received within said housing and not integral to said flexible housing; and
   c) structure defining at least one access port through said housing.

2. The device according to claim 1 wherein said flexible housing is comprised of a gas permeable material.

3. The device according to claim 2 wherein said gas permeable material is comprised of at least two different materials, each material differing in its oxygen, carbon dioxide or moisture vapor permeability.

4. The device according to claim 2 wherein said gas permeable, liquid impermeable material of said housing is comprised of dimethyl silicone.

5. The device according to claim 2 wherein said gas permeable material is comprised of PTFE.

6. The device according to claim 1, wherein said upper wall and lower walls, have substantially the same footprint as a cell attachment matrix.

7. The device according to claim 1 wherein only one access port is present.

8. The device according to claim 1, including a cutting die and means for positioning said die whereby said cutting die is driven through said cell attachment matrix when the distance between the upper wall and lower walls is reduced.

9. The device according to claim 1 wherein said flexible housing has at least one wall that is substantially parallel to said cell attachment matrix for the purpose of allowing uniform cell seeding or uniform soluble gas concentration across the surface of said cell attachment matrix.

10. The device according to claim 9 wherein said one wall substantially parallel to said cell attachment matrix presents a surface facing said cell attachment matrix, said surface presenting at least one projection for the purpose of preventing one said wall from contacting said cell attachment matrix.

11. The device according to claim 9, including an outer housing wherein said one wall substantially parallel to said cell attachment matrix is interposed between said outer housing and said cell attachment matrix and whereby said outer housing includes interface means with said one wall substantially parallel to said cell attachment in order to prevent said one wall substantially parallel to said cell attachment matrix from contacting said cell attachment matrix.

12. A device for cryopreservation including:
a) a cryopreservation enclosure;
b) a bioreactor received within said cryopreservation enclosure, said bioreactor comprised of a gas permeable material;
c) a gas compartment located between said cryopreservation enclosure and said bioreactor;
d) a structure defining at least one access port to said bioreactor;
e) a structure defining at least one gas compartment access port to said gas compartment.

13. The device according to claim 8, wherein said cutting die is configured to cut more than one section from cell attachment matrix when the distance between said upper and lower walls is reduced.

14. The device according to claim 1, including a clamp attached to said flexible housing and said clamp attached to said cell attachment matrix in order to retain cell attachment matrix in a desired position within said flexible housing.

15. The device according to claim 14, including an outer housing in contact wilt said upper and said lower flexible walls.

16. The device according to claim 1, including a matrix holder in contact with the lower surface of said cell attachment matrix, said matrix holder elevated by legs above said lower wall such that a volume of space is created between said cell attachment matrix and said lower wail and said cell attachment matrix and said upper wall.

17. The device according to claim 16, including a lower cell attachment matrix residing between said cell attachment matrix and said lower wail.

18. The device according to claim 1, including a frame within said flexible housing, said cell attachment matrix secured to said frame.

19. The device according to claim 1, wherein a tissue construct matrix is oriented generally parallel to said upper wall and located a distance above said lower wall such that a first compartment is created between said cell attachment matrix and said upper wall and a second compartment is created between said cell attachment matrix and said lower wall.

20. The device according to claim 19, including a lower cell attachment matrix in said second compartment.

* * * * *